United States Patent
Azimpour et al.

(10) Patent No.: US 9,861,464 B2
(45) Date of Patent: Jan. 9, 2018

(54) CARDIO-EMBOLIC STROKE PREVENTION

(71) Applicant: Regents of the University of Minnesota, Minneapolis, MN (US)

(72) Inventors: Farzad Azimpour, Houston, TX (US); Robert F. Wilson, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 231 days.

(21) Appl. No.: 14/391,639

(22) PCT Filed: Mar. 15, 2013

(86) PCT No.: PCT/US2013/032222
§ 371 (c)(1),
(2) Date: Oct. 9, 2014

(87) PCT Pub. No.: WO2013/154765
PCT Pub. Date: Oct. 17, 2013

(65) Prior Publication Data
US 2015/0073469 A1    Mar. 12, 2015

Related U.S. Application Data

(60) Provisional application No. 61/623,989, filed on Apr. 13, 2012.

(51) Int. Cl.
*A61F 2/01* (2006.01)
*A61F 2/06* (2013.01)
(Continued)

(52) U.S. Cl.
CPC ............... *A61F 2/013* (2013.01); *A61F 2/06* (2013.01); *A61F 2/82* (2013.01); *A61F 2/01* (2013.01);
(Continued)

(58) Field of Classification Search
CPC .... A61F 2/013; A61F 2/02; A61F 2/06; A61F 2/82; A61F 2/89; A61F 2/915; A61F 2/01;
(Continued)

(56) References Cited

U.S. PATENT DOCUMENTS 6,499,487 B1   12/2002   McKenzie et al.
6,866,680 B2 *  3/2005   Yassour ............ A61F 2/01
                                                623/1.15
(Continued)

FOREIGN PATENT DOCUMENTS

EP        0804908 A1    5/1997
WO     2009070624 A1    6/2009

OTHER PUBLICATIONS

International Preliminary Report on Patentability from Counterpart International Application No. PCT/US2013/03222, dated Aug. 11, 2014, 11 pp.
(Continued)

*Primary Examiner* — Jocelin Tanner
(74) *Attorney, Agent, or Firm* — Shumaker & Sieffert, P.A.

(57) ABSTRACT

An embolic protection device comprises an intravascular flow-interactive surface supported by an expandable, substantially cylindrical frame, wherein the frame is configured to expand and engage the luminal surface of the ascending aortic arch, wherein said frame defines a longitudinal channel generally parallel to predominant blood flow vectors, and wherein a flow-modulating element is configured to alter fluid dynamics in a manner that redirects the cranial trajectory of embolic particles originating from the heart through and beyond the longitudinal channel. The embolic protection device may also comprise a plurality of independent or interconnected flow-modulating elements serially spaced apart along the longitudinal axis of the primary (Continued)

vessel. The interstitial space between flow-modulating elements allows blood flow passage between one another in a direction generally perpendicular to the longitudinal channel. The open central channel allows interval passage and manipulation of transcatheter instruments while maintaining the integrity of radially positioned flow-modulating surfaces.

22 Claims, 23 Drawing Sheets

(51) Int. Cl.
    *A61F 2/82*     (2013.01)
    *A61F 2/89*     (2013.01)
    *A61F 2/915*     (2013.01)

(52) U.S. Cl.
    CPC ............... *A61F 2/89* (2013.01); *A61F 2/915* (2013.01); *A61F 2002/016* (2013.01); *A61F 2002/068* (2013.01); *A61F 2002/821* (2013.01); *A61F 2210/0014* (2013.01); *A61F 2230/0013* (2013.01); *A61F 2230/0034* (2013.01); *A61F 2230/0069* (2013.01); *A61F 2230/0091* (2013.01)

(58) Field of Classification Search
    CPC ...... A61F 2/856; A61F 2/04; A61F 2002/016; A61F 2002/018; A61F 2002/91583; A61F 2002/91541; A61F 2002/9155; A61F 2002/821; A61F 2230/0091; A61F 2230/0069; A61F 2230/0034; A61F 2230/0013; A61F 2210/0014
    See application file for complete search history.

(56) References Cited

U.S. PATENT DOCUMENTS

| | | | |
|---|---|---|---|
| 7,232,453 B2 | 6/2007 | Shimon | |
| 7,604,650 B2 | 10/2009 | Bergheim | |
| 7,758,606 B2 | 7/2010 | Streeter et al. | |
| 8,062,324 B2 | 11/2011 | Shimon et al. | |
| 2004/0010307 A1 | 1/2004 | Grad et al. | |
| 2004/0073253 A1 | 4/2004 | Morrill et al. | |
| 2004/0167613 A1 | 8/2004 | Yodfat et al. | |
| 2004/0215167 A1* | 10/2004 | Belson | A61F 2/01 604/526 |
| 2006/0287668 A1 | 12/2006 | Fawzi et al. | |
| 2008/0065145 A1 | 3/2008 | Carpenter | |
| 2008/0140110 A1* | 6/2008 | Spence | A61F 2/06 606/200 |
| 2008/0269871 A1 | 10/2008 | Eli | |
| 2009/0326575 A1 | 12/2009 | Galdonik et al. | |
| 2010/0076482 A1 | 3/2010 | Shu et al. | |
| 2010/0106180 A1* | 4/2010 | Strother | A61F 2/82 606/200 |
| 2010/0179583 A1 | 7/2010 | Carpenter et al. | |
| 2010/0179584 A1 | 7/2010 | Carpenter et al. | |
| 2010/0179585 A1 | 7/2010 | Carpenter et al. | |
| 2010/0179647 A1 | 7/2010 | Carpenter et al. | |
| 2010/0185231 A1 | 7/2010 | Lashinski | |
| 2010/0191276 A1 | 7/2010 | Lashinski | |
| 2010/0211095 A1 | 8/2010 | Carpenter | |
| 2010/0217303 A1 | 8/2010 | Goodwin | |
| 2010/0228280 A1 | 9/2010 | Groothuis et al. | |
| 2010/0312268 A1 | 12/2010 | Belson | |
| 2011/0022076 A1 | 1/2011 | Lashinski | |
| 2011/0106137 A1 | 5/2011 | Shimon | |
| 2011/0282379 A1 | 11/2011 | Lee et al. | |
| 2011/0313445 A1 | 12/2011 | Galdonik et al. | |

OTHER PUBLICATIONS

Invitation to Pay Additional Fees from Counterpart International Application No. PCT/US2013/032222, dated Jun. 18, 2014, 6 pp.
Reply to Written Opinion dated Feb. 3, 2014, from Counterpart International Application No. PCT/US2013/032222, dated May 2, 2014, 25 pp.
International Search Report and Written Opinion from Counterpart International Application No. PCT/US2013/032222, dated Feb. 3, 2014, 15 pp.

* cited by examiner

CARDIO-EMBOLIC STROKE PREVENTION

This application is a national stage entry under 35 U.S.C. §371 of PCT Application No. PCT/US2013/032222, filed Mar. 15, 2013, which claims the benefit of U.S. Provisional Application No. 61/623,989, filed Apr. 13, 2012. The entire contents of PCT Application No. PCT/US2013/032222 and U.S. Provisional Application No. 61/623,989 are incorporated herein by reference.

TECHNICAL FIELD

The invention relates to implantable medical devices and, more particularly, vascularly-implantable medical devices for preventing cardio-embolic stroke.

BACKGROUND

Stroke is the third leading cause of death in the United States and otherwise a frequently disabling neurologic condition. The American Heart Association estimates an annual stroke incidence of 500,000 new patients and prevalence of 4 million stroke survivors. Many of these patients require chronic rehabilitation and specialized care, and frequently require long-term hospitalization.

Cerebral embolic stroke represents approximately 10-24% of all stroke types, the remainder of which are atherothrombotic or hemorrhagic in origin. Mechanisms responsible for particle embolization from cardiac structures to the cranial circulation include thrombosis from flow stagnation secondary to arrhythmias and post-myocardial infarction left ventricular dysfunction, intracardiac mechanical prosthesis-blood interface coagulation activation, infective or non-infective endocarditis, and instrument thrombosis related to left-sided endocardial ablations, valvuloplasties, and transcatheter valve replacements.

Current therapies targeting the pro-thrombotic state of atrial arrhythmias include chronic oral anticoagulation and more recently mechanical isolation of the thrombus-prone left atrial appendage for patients deemed to have elevated bleeding risk. Mainstay oral anticoagulation involves variable-dose daily medication with weekly to monthly serum level surveillance for therapeutic effect. Novel anticoagulation with set dosing and no blood level surveillance has recently entered clinical practice, although currently no reversal agents exist in the event of catastrophic bleeding complications. Left atrial appendage occlusion or isolation devices target the essential elimination of the structure most recognized as a culprit region with flow stagnation in atrial arrhythmias, ultimately leading to thrombus formation and potential dislodgment and embolization to the cranial circulation, i.e. stroke. These devices either fill the structural void of the appendage from an intracardiac plug approach, or ligate the segment from a combined epicardial approach such as that augmented with magnetic guidance.

Surgically implanted mechanical prosthetic intracardiac valves require lifelong oral anticoagulation to halt the coagulation cascade and resulting thrombosis activated at the device interface. Under certain clinical circumstances such as bleeding, when reversal of anticoagulation is required to prevent excessive blood loss, the mechanical device in contact with the patient's circulating blood becomes particularly susceptible to thrombosis, and again, embolization leading to potential stroke.

Transcatheter aortic valve replacement or implantation (TAVR/TAVI) is gaining popularity as a minimally invasive alternative method for treating severe aortic stenosis (AS) in patients deemed to have prohibitive surgical risk. TAVR is a procedure whereby a catheter-loaded bio-prosthetic aortic valve is delivered either percutaneously via peripheral arteries or surgically via a mini-thoracotomy with trans-apical or trans-aortic approach to the native aortic valve region, following balloon valvuloplasty. The most significant adverse outcome associated with this approach is stroke, both at the time of procedure and up to 2 years post-procedure, despite dual antiplatelet therapy.

The Placement of Aortic Trans-catheter Valves (PARTNER) trial, published in 2010 in The New England Journal of Medicine, found that in high-risk patients with symptomatic severe AS, including those deemed unsuitable candidates for surgery, TAVR, as compared to standard therapy (i.e. balloon valvuloplasty), significantly reduced cardiac symptoms, repeat hospitalization, and all-cause mortality. However, this trial revealed a higher incidence of major strokes and vascular events with TAVR, at both thirty days and one year post-implant. Follow-up data from this trial has demonstrated persisting stroke risk beyond 2 years. Both subclinical athero-embolization (detected by diffusion-weighted magnetic resonance imaging of the brain) and clinically evident stroke are potential complications of TAVR, and carry the greatest implications in patient outcome and peri-procedural cost from additional care and hospitalization. Proposed mechanisms for increased risk of embolic events during and after TAVR include the aortic luminal trauma during catheter and device transit, balloon valvuloplasty, deployment-related mechanical disruption of the aorta and native aortic valve causing fragmentation and embolization, potential valvular micro-thrombi, and atrial fibrillation (AF) following TAVR.

Additionally, left-sided or systemic circulation endocardial ablation procedures target elimination of electrophysiologic channels, pathways, and foci responsible for arrhythmias including atrial fibrillation, atypical left-sided flutter, atrial tachycardia, bypass tracts, and ventricular tachycardia. These procedures require either trans-septal or trans-aortic instrument transit to targeted ablation site, exposing instrument surfaces to blood, and yielding potential for thrombus formation and embolic events.

SUMMARY

In general, embolic protection devices and methods for using such devices are described. An embolic protection device engages the inner wall of a blood vessel, such as the aortic arch, and includes one or more embolic flow-modulating elements, which may comprise angled flow-modulating or deflective surfaces. The embolic protection device defines a longitudinal passageway through the device, and the flow-modulating elements modulate blood flow such that emboli shift trajectory based on modulated blood flow streamlines. The shift in embolic trajectory may occur with or without contact with the surface of a flow-modulating element. The emboli pass through the device via the longitudinal passageway, downstream and away from the cranial circulation. Blood may pass through the device in a direction generally transverse to the longitudinal passageway, e.g., to enter branches of the primary blood vessel. The longitudinal passageway is sized so that catheters or other instruments for performing cardiac procedures, e.g., aortic valvuloplasty, TAVR, coronary angiography or intervention, or endocardial ablation, may pass through the passageway while the protection device is seated in its functional position. The embolic protection device may remain implanted after such a procedure is performed, e.g., chronically.

In one example, an embolic protection device comprises an expandable and substantially cylindrical frame. The frame is configured to expand to engage an inner wall of a blood vessel. The frame defines a longitudinal passageway through the frame when expanded, and wherein the expanded frame includes an inner circumference. The embolic protection device further comprises a flow-modulating element within the frame. The flow-modulating element extends around a portion of the inner circumference of the frame less than the entire inner circumference. The flow-modulating element comprises a leading surface and a trailing surface, and the leading surface and the trailing surface form a hydrofoil shape.

In another example, an embolic protection device comprises an expandable and substantially cylindrical frame. The frame is configured to expand to engage an inner wall of a blood vessel. The frame defines a longitudinal passageway through the frame when expanded. The embolic protection device further comprises a plurality of embolic flow-modulating elements within the frame. The embolic flow-modulating elements are spaced apart and located at respective longitudinal, e.g., axial or along the longitudinal axis, positions along the frame. The spacing apart of the flow-modulating elements allows blood to pass between the flow-modulating elements and through the frame in a direction generally transverse to the longitudinal passageway. The flow-modulating elements are configured to deflect emboli and direct the emboli through the frame via the longitudinal passageway.

In another example, an embolic protection device comprises an expandable and substantially cylindrical frame configured to expand to engage an inner wall of a blood vessel, and a helical embolic flow-modulating element within the frame. The flow-modulating element has an outer diameter and an inner diameter. The inner diameter defines a longitudinal passageway through the frame when the frame is expanded. The helical embolic flow-modulating element comprises a deflective surface between the outer diameter and the inner diameter, the deflective surface configured to face the flow of blood within the vessel and deflect emboli and direct the emboli through the frame via the longitudinal passageway when the embolic protection device is implanted within the vessel. The helical embolic flow-modulation allows blood to pass through the frame in a direction generally transverse to the longitudinal passageway.

In another example, a method comprises inserting an embolic protection device into a common vascular access, deploying an embolic protection device to engage the inner wall of a target vessel, inserting a procedure instrument into the common vascular access, advancing the procedure instrument through the longitudinal passageway of the embolic protection device and to a procedure target, performing a procedure using the procedure instrument with embolic protection device engaged to the inner wall of the target vessel, and withdrawing the procedure instrument through the longitudinal passageway of embolic protection device. The embolic protection device may remain implanted chronically, with the potential for later retrieval.

The details of one or more examples are set forth in the accompanying drawings and the description below. Other features, objects, and advantages will be apparent from the description and drawings, and from the claims.

DETAILED DESCRIPTION

This disclosure describes devices, systems, and techniques for stroke prevention. In various examples, one or more flow-modulating elements is implanted within a patient's aortic arch. The flow-modulating element interrupts the flow of blood through the patient's primary vessel (i.e. aortic arch) while still allowing blood to pass freely through the vessel to the cranially-directed branch vessels and beyond to the rest of the body. When laminar blood flow encounters the modulating element's surface, blood flow streamlines converge at the leading edge of the flow-modulating element and then diverge as the blood flows along the trailing edge of the flow-modulating element. A particle, such as an embolus, that is traveling in a particular streamline shifts to an adjacent streamline and continues downstream past a branch vessel ostium rather than following a streamline into said branch vessel. The shift in trajectory of the particle may occur with or without direct contact with the surface of the flow-modulating element.

In some examples, a flow-modulating element is implanted on the greater curvature of the aortic arch proximal to the brachiocephalic takeoff. A stent-like frame may support the flow-modulating element. In some examples, the flow-modulating element may encircle the inner aspect of the frame, resulting in a deflective surface that is symmetrical around the vessel. In some examples, the flow-modulating element covers less than, e.g., approximately half of, the circumference of the frame, resulting in a deflective surface that is radially asymmetrical within the vessel. In some examples, an embolic protection device may include a series of axially oriented rings, each ring including a flow-modulating surface. One or more of the flow-modulating elements may partially block one or more ostia.

In various examples, the embolic protection device may be implanted temporarily within a patient. For example, the device may be implanted prior to a cardiac procedure, such as TAVR or endocardial ablation. The embolic protection device may help prevent stroke from emboli resulting from the cardiac procedure. After the procedure is completed, the embolic protection device may also be removed.

In other examples, the embolic protection device may be permanently implanted. For example, the embolic protection device may be implanted in a patient at increased long-term risk for stroke. In some examples, the frame of the embolic protection device may be configured to allow endothelial cellular growth to further anchor the device.

Figure 1A:
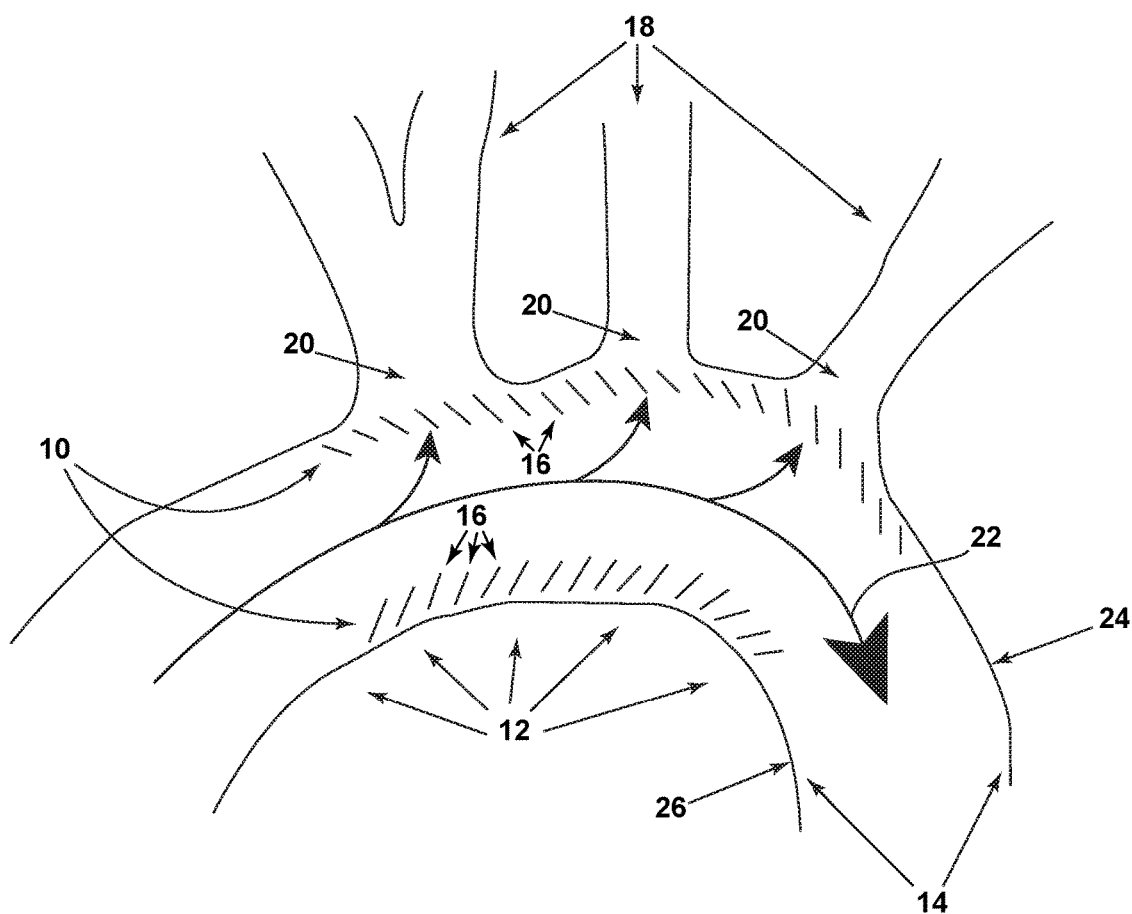
FIG. 1A is a conceptual cross-sectional diagram illustrating an example embolic protection device implanted within the aortic arch.

FIG. 1A is a conceptual cross-sectional diagram illustrating an example embolic protection device 10 implanted within the aortic arch 12. Embolic protection device 10 engages the inner wall 14 of aortic arch 12. In some examples, embolic protection device 10 may be compressed and loaded onto a catheter-tip, having a smaller initial profile, e.g., diameter, for delivery through the vasculature to a target vascular location, e.g., the aortic arch. Embolic protection device 10 may then expand to engage the inner wall 14 of the target vessel. Embolic protection device 10 may, as examples, be expanded by inflation of a balloon or other inflatable element, or by being released from a restraining element that maintains the embolic protection device 10 in its compressed state.

In the illustrated example, embolic protection device 10 comprises a plurality of flow-modulating elements 16. In the illustrated example, embolic protection device 10 is positioned such that flow-modulating elements 16 divert emboli from entering the cranially-supplying branch arteries 18 from aortic arch 12. Embolic protection device 10 is positioned such that at least some of flow-modulating elements 16 partially block ostia 20 of the cranially-supplying branch arteries 18. However, flow-modulating elements 16 are spaced such that blood may flow between the elements and enter the cranially-supplying branch arteries via the ostia. When deployed in the aortic arch, the device may partially cover the ostia of the brachiocephalic trunk, left common carotid, and left subclavian arteries, or any anatomic variant of such blood vessels. The series of flow-modulating rings may act to protect the distal cranial circulation from particulate or thromboembolic matter that would otherwise follow fluid flow cranially and, potentially, result in stroke.

Embolic protection device 10 and embolic flow-modulating elements 16 are configured, e.g., sized, to provide a longitudinal passageway 30 (FIG. 1B) through the embolic protection device. Blood flow 22 to the systemic circulation may occur through the longitudinal passageway 30. Furthermore, flow-modulating elements 16 are configured to deflect emboli approaching the ostia 20 such that the emboli proceed through the longitudinal passageway 30 rather than entering the ostia 20. Flow-modulating elements 16 may comprise an angled flow-modulating surface to deflect the emboli into the longitudinal passageway 30.

Figure 1B:
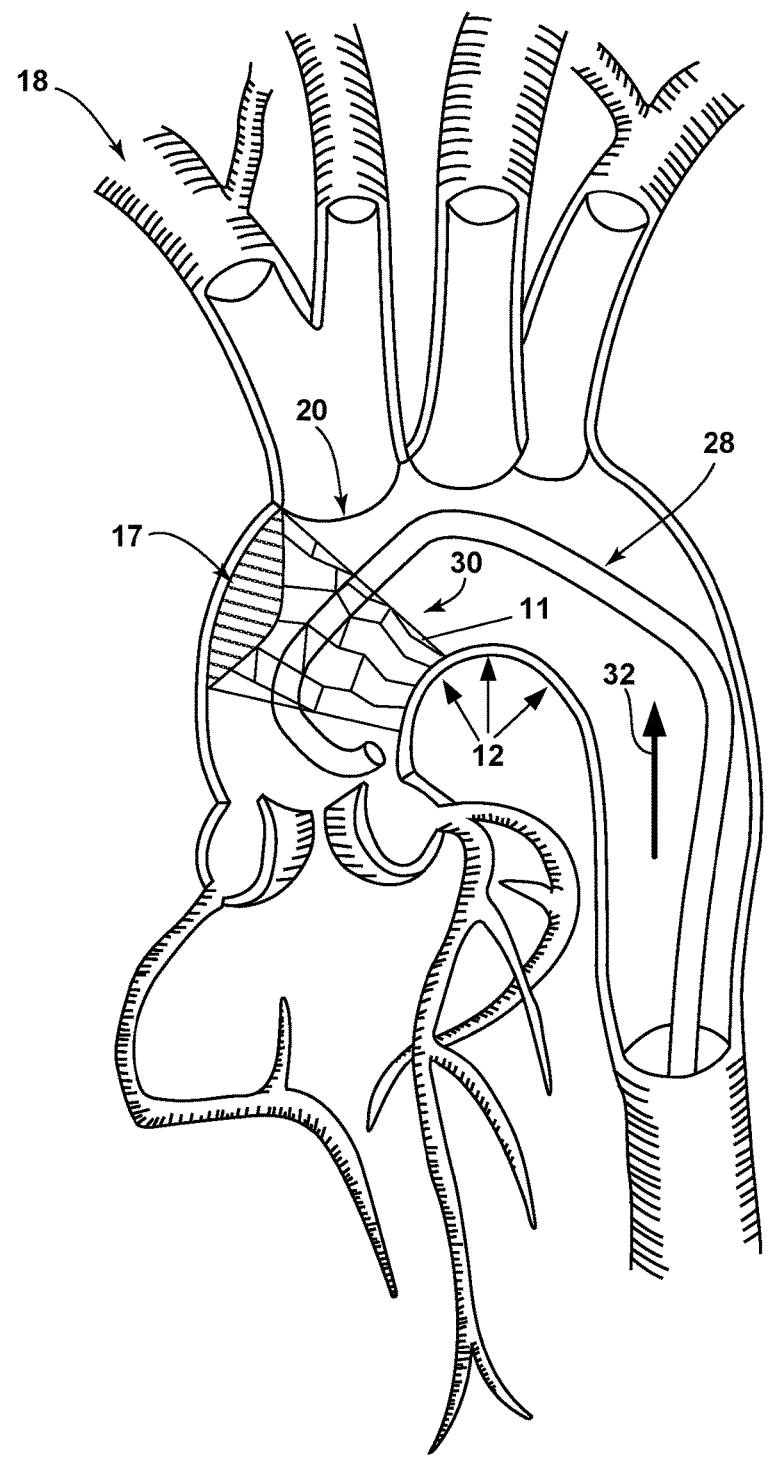
FIG. 1B is a conceptual cross-sectional diagram illustrating an example embolic protection device in conjunction with an instrument.

FIG. 1B is a conceptual cross-sectional diagram illustrating an embolic protection device 11 in conjunction with a cardiac-directed procedure instrument 28. As illustrated in FIG. 1B, procedure instrument 28 may be advanced through longitudinal passageway 30 to the heart in the direction of arrow 32. Embolic protection device 11 and flow-modulating element 11 may be configured, e.g., sized, such that longitudinal passageway 30 is large enough to allow a variety of procedure instruments 28 to pass freely through embolic protection device 11 via passageway 30. Example procedure instruments 28 include guidewires, coronary catheters, sheaths, balloons, stents, or any instrument used for cardiac procedures, such as TAVR, valvuloplasty, or endocardial ablation.

In some examples, embolic protection device 11 may be positioned within the aortic arch 12 so that flow-modulating element 17 is directly proximal to an ostium 20. The trailing edge of the flow-modulating element may be positioned close to the edge of ostium 20.

Figure 2A:
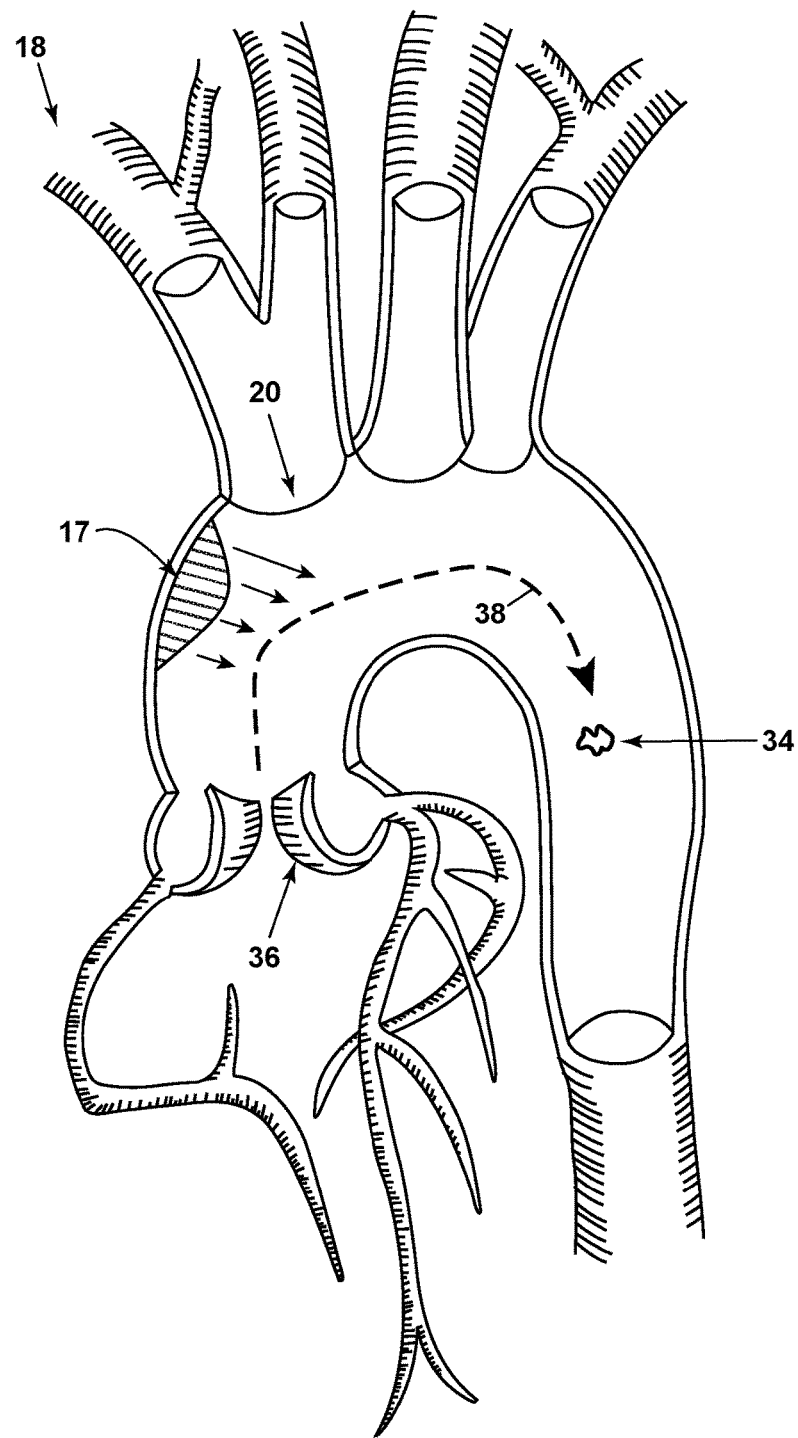
FIG. 2A is a conceptual cross-sectional diagram illustrating the embolic protection device of FIG. 1B in conjunction with an embolus.

FIG. 2A is a conceptual cross-sectional diagram illustrating flow-modulating element 17 of FIG. 1B in conjunction with an embolus 34. As illustrated in FIG. 2A, embolus 34 may enter the aortic arch via the aortic valve 36, or due to a procedure performed on or proximal to aortic valve 36. Embolus 34 then travels through aortic arch 12 and toward ostia 20 (FIGS. 1A and 1B) of cranially-supplying branches 18 via path 38.

Figure 7A:
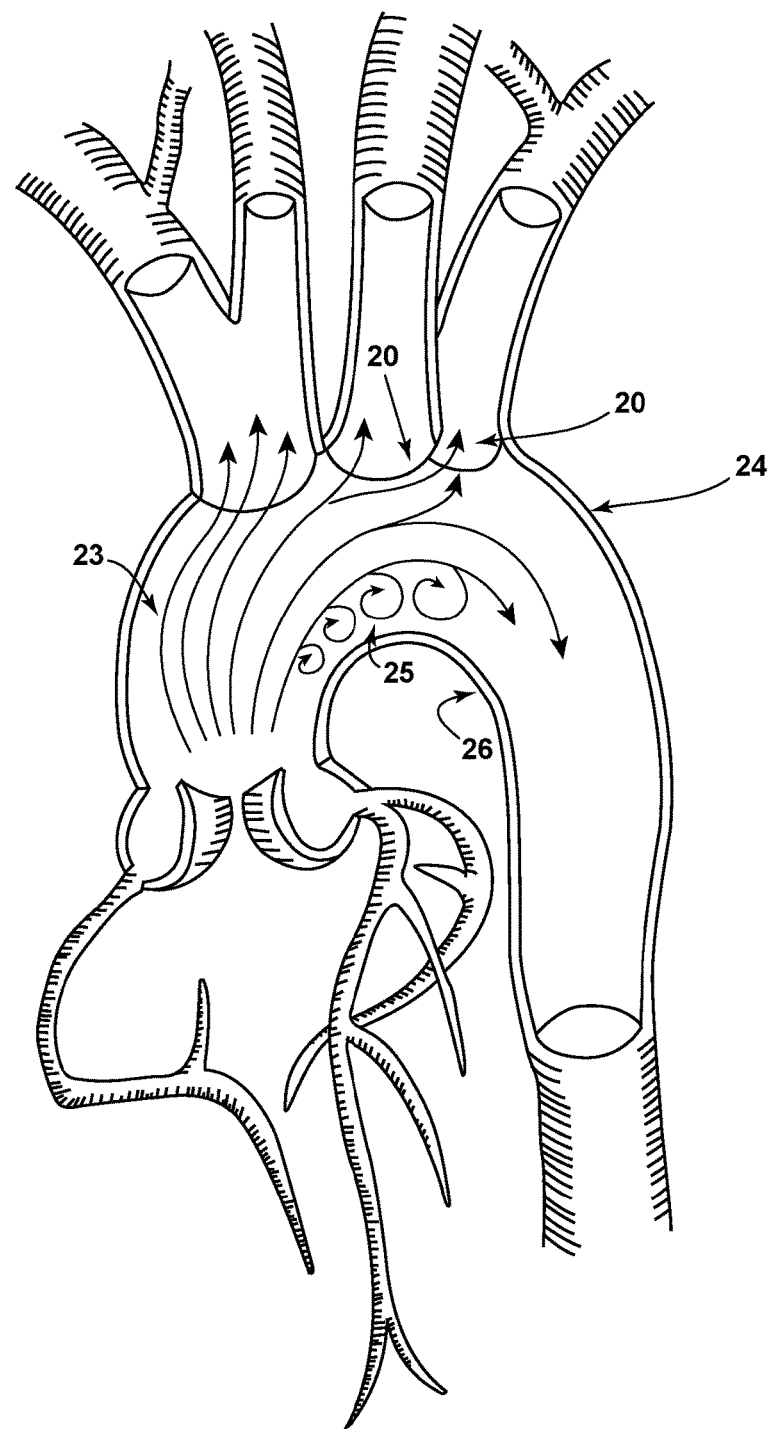
FIG. 7A is a conceptual diagram illustrating blood flow in an aortic arch.

According to Bernoulli's principle, as laminar fluid flow approaches a curve, velocity at the greater or outer curvature (concavity) 24 (FIG. 1A) is slower, while velocity at the lesser or inner curvature (convexity) 26 (FIG. 1A) is faster. Slower velocity is accompanied by higher pressure, while faster velocity is accompanied by lower pressure. Additionally, slower velocity is accompanied by relatively more laminar flow (relatively lower Reynolds number), while faster velocity is accompanied by more turbulent flow (relatively higher Reynolds number). Ultimately, it is the pressure gradient formed from the outer curvature 24 to the inner curvature 26 that drives flow 22 (FIG. 1A) around the curve of the aorta to supply blood to the body. Flow is additionally driven by a pressure gradient formed from the outer curvature of the aortic arch towards the intracranial circulation. Given the curvature and multiple takeoff points from the main channel of the aorta into the ostia 20 of cranially-supplying vessels 18, vortices of flow at divergence points additionally factor into the fluid dynamics of the aortic arch 12. Streamlines illustrating blood flow through the aortic arch before implantation of a flow-modulating element is shown in FIG. 7A, and discussed below.

As embolus 34 exits the heart, it is propelled by the systolic pulse on a trajectory toward the aortic arch 12. More particularly, embolus 34 preferentially follows path 38 initially directed toward the outer concave curvature (greater diameter) 24 of the aortic arch 12 toward the location of cranial-supplying arterial ostia 20, then shifts away from said ostia, continuing downstream away from the brain. In a mechanically-unprotected scenario, pressure at the aortic arch directs flow, and may direct the embolus, down a pressure gradient, through a cranial-supplying arterial ostium, and toward the brain, leading to stroke.

Embolic protection devices as described herein may be deployed prior to or during medical procedures that may impose elevated risk of embolic stroke, such as TAVR, valvuloplasty, or endocardial ablation. Embolic protection devices may also be deployed in patients with elevated stroke risk from arrhythmia, e.g., AF, deemed otherwise high-risk candidates for anticoagulation. An embolic protection device may also be deployed within or adjacent a medical device that increases the risk of embolic stroke, such as a ventricular assist device (VAD).

An example application for embolic protection devices as described herein is aortic arch implantation prior to TAVR and/or valvuloplasty. Embolic protection devices may be implanted chronically or otherwise for an extended period of time, e.g., remaining implanted after the TAVR or valvuloplasty procedure. The longitudinal passageway of the embolic protection device facilitates such long duration implantation in that the passageway allows interval access through embolic protection device 10 with wires, catheters and other instruments, both during the procedure, and for any subsequent procedures that occur while the device remains implanted. Ultimately, by allowing device delivery just prior to and via the same access point as TAVR or valvuloplasty, faster overall procedure times are achieved, with the temporal benefit of "protected" cerebral circulation throughout the entirety of the procedure and beyond, into the extended peri-procedural risk period for stroke.

Another application of the embolic protection devices described herein is stroke prophylaxis for the population of patients with cardiac arrhythmias, such as AF, that predispose them to elevated risk of thromboembolic events. Currently, such patients are risk-stratified for long-term thromboembolic risk based on the "CHADS2" scoring system, which stratifies patients' stroke risk based on a score that indicates that recommended level of anticoagulation therapy to reduce patients' stroke risk. In some patients with elevated CHADS2 scores, which would otherwise indicate recommended anticoagulation, the bleeding risk from anticoagulation equals or outweighs their stroke risk.

Embolic protection devices as described herein may avoid interfering with cerebral blood flow and relative pressure, e.g., due to the spacing between flow-modulating elements. The longitudinal passageway of embolic protection devices as described herein may provide a relatively unobstructed passage of catheters and other instruments through and beyond the device without disrupting the positioning and function of the embolic protection device. Additionally, the overall structure of embolic protection devices as described herein may be more fixed and less compliant, and thus more applicable to an arterial pressure environment. Embolic protection devices may nevertheless conform to a variety of vessels, such as the aortic arch.

Figure 8:
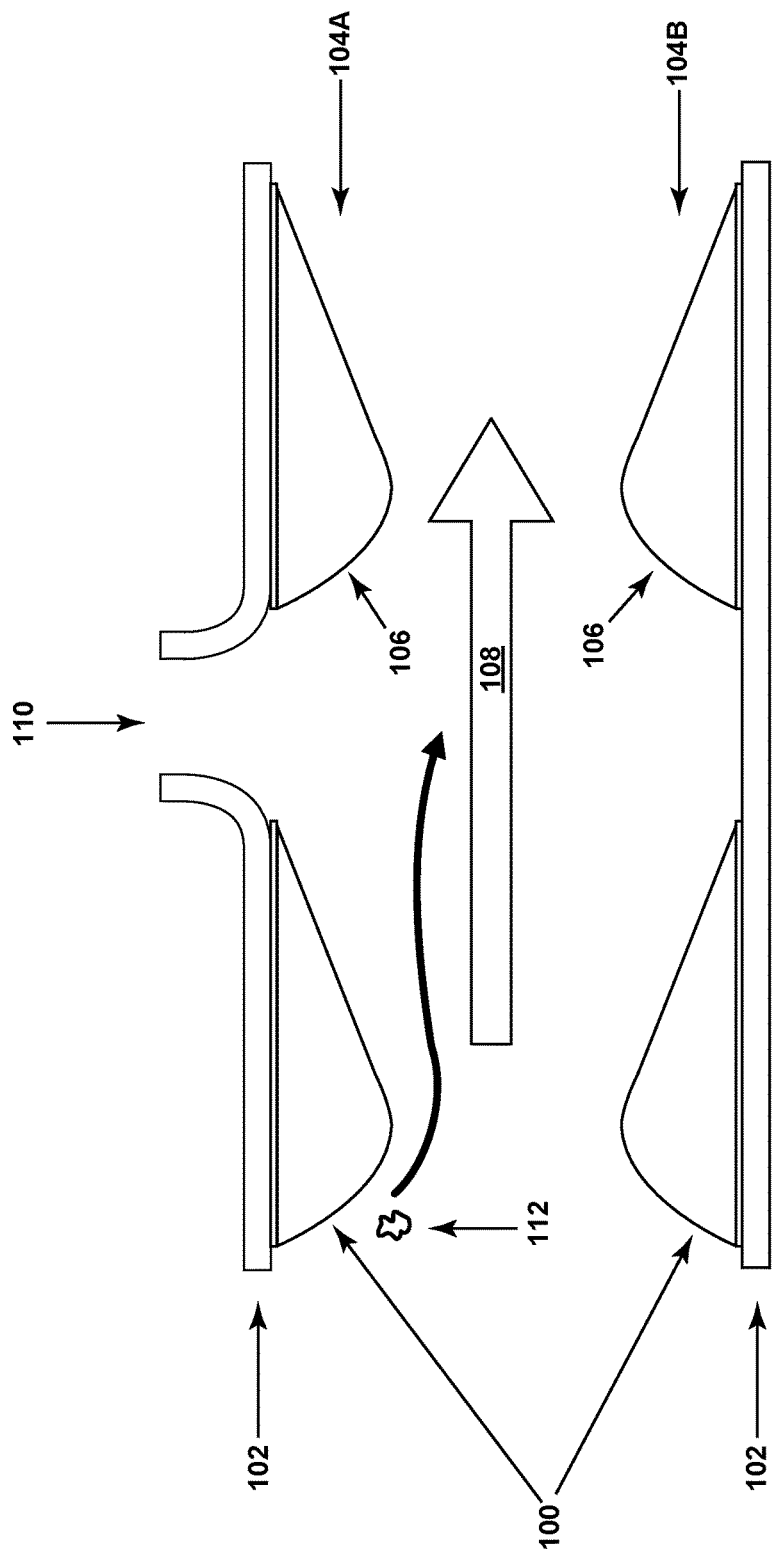
FIG. 8 is a conceptual diagram illustrating another example embolic protection device implanted within a blood vessel.
Figure 9:
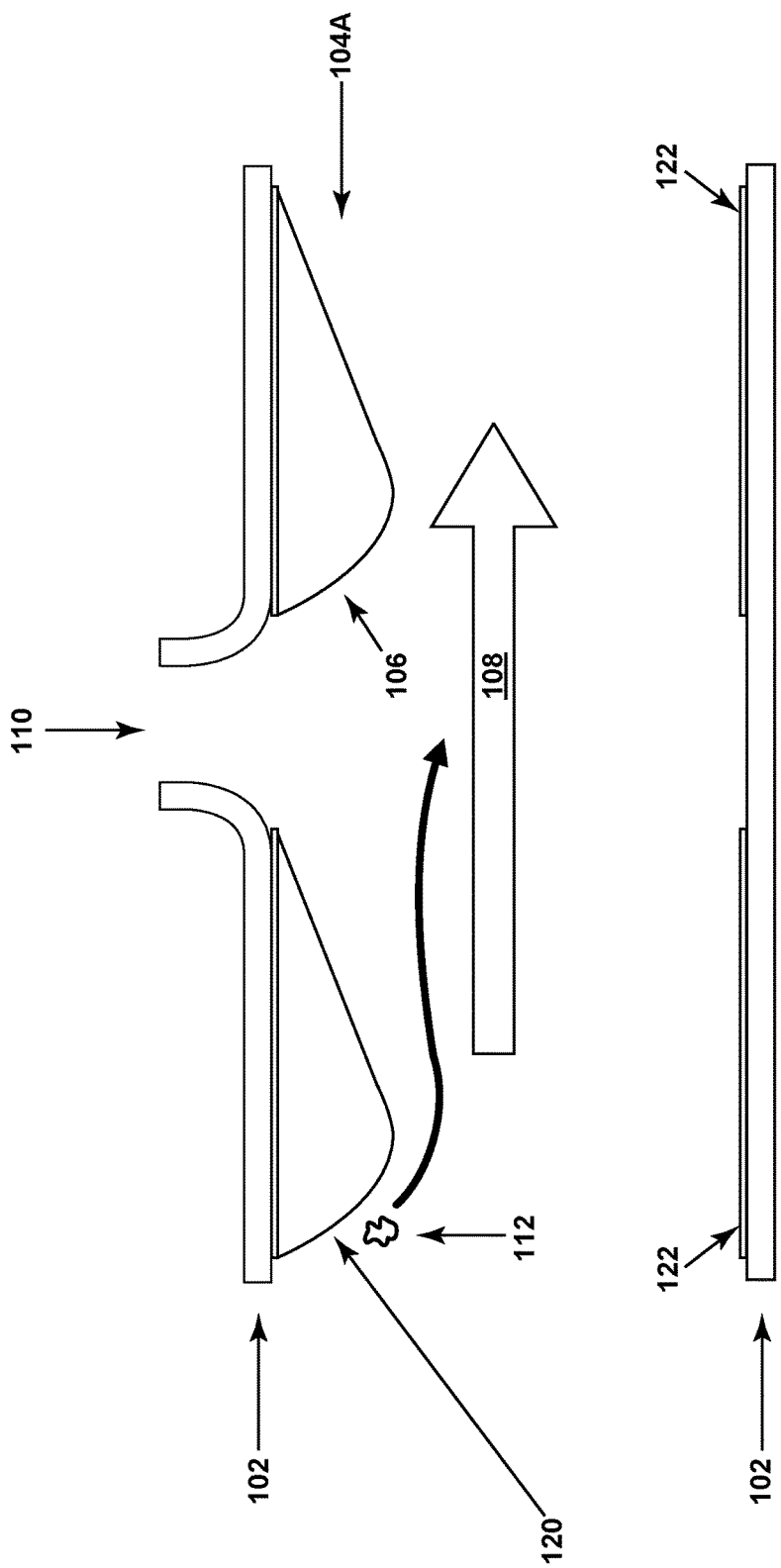
FIG. 9 is a conceptual diagram illustrating another example embolic protection device implanted within a blood vessel.

In some examples, the embolic protection devices are radially symmetric, which may facilitate implantation, obviating the need for a particular rotational orientation of the device in the vessel, e.g., aortic arch. In other examples, embolic protection devices may only have deflective surfaces at the superior aspect of the device, e.g., along greater curvature of the aortic arch 24 (FIG. 1A) proximal to the cranially-supplying arterial ostia. The portion of the device proximal to the lesser curvature of the aortic arch 26 (FIG. 1A) may be relatively flat and free of elements protruding into the longitudinal passageway. FIGS. 8 and 9, discussed below, show a radially symmetrical embolic protection device and a radially asymmetrical embolic protection device, respectively.

Figure 2B:
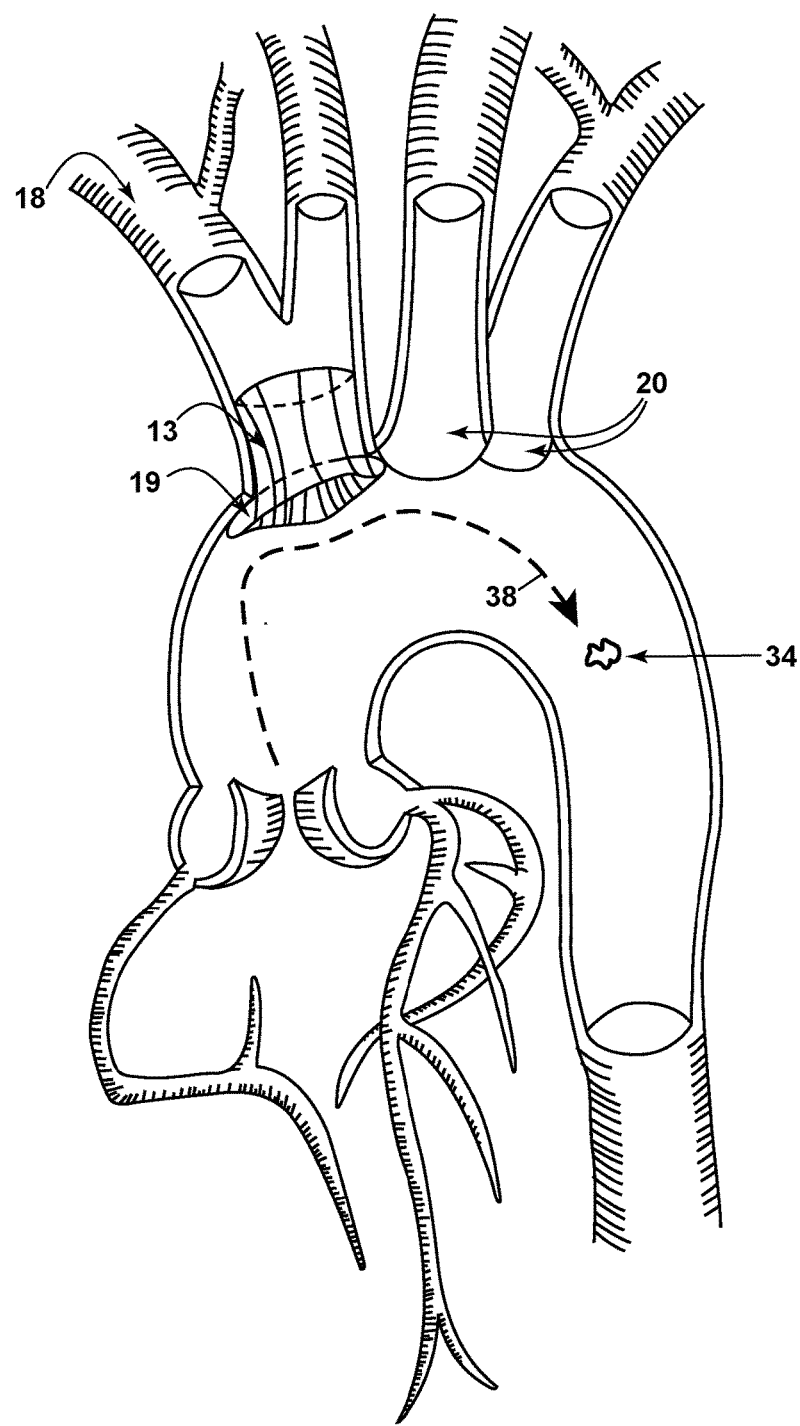
FIG. 2B is a conceptual cross-sectional diagram illustrating another example embolic protection device in conjunction with an embolus.

FIG. 2B is a conceptual cross-sectional diagram illustrating another example embolic protection device 13 in conjunction with an embolus. Embolic protection device 13 is implanted in a branch vessel 18, and flow-modulating element 19 encircles ostium 20. As embolus 34 exits the heart, it is propelled by the systolic pulse on a trajectory toward the aortic arch 12. More particularly, embolus 34 preferentially follows path 38 directed toward the outer concave curvature (greater diameter) 24 of the aortic arch 12, and toward the location of cranial-supplying arterial ostia 20. In a mechanically-unprotected scenario, pressure at the aortic arch directs flow, and may direct the embolus, down a pressure gradient, through a cranial-supplying arterial ostium, and toward the brain, leading to stroke.

In the example of FIG. 2B, flow-modulating element 19 deflects the path of embolus 34 way from ostia 20, while still allowing blood to flow through branch vessel 18. In the example of FIG. 2B, embolic protection device 13 may be a cuffed sleeve, wherein the cuff is flow-modulating element 19. Embolic protection device 13 may be self-expanding or a balloon-expandable stent. As shown in FIG. 2B embolic protection device 13 may be deployed at a proximal segment of a cranially-directed vessel 18. Flow-modulating element 13 may be a circumferential cuff or bumper extending around ostium 20 into the lumen of the primary vessel (such as the aortic arch). The extension into the primary vessel acts as flow-modulating element 19. In addition, the flow-modulating element may anchor the embolic protection device to prevent distal dislodgment toward the brain. The orientation of embolic protection device 12 may provide 360-degree flow modulation surrounding vessel ostium 20, such that flow that would otherwise facilitate embolization of threatening particles traveling with diastolic retrograde aortic trajectory is also disrupted and redirected.

Figure 3A:
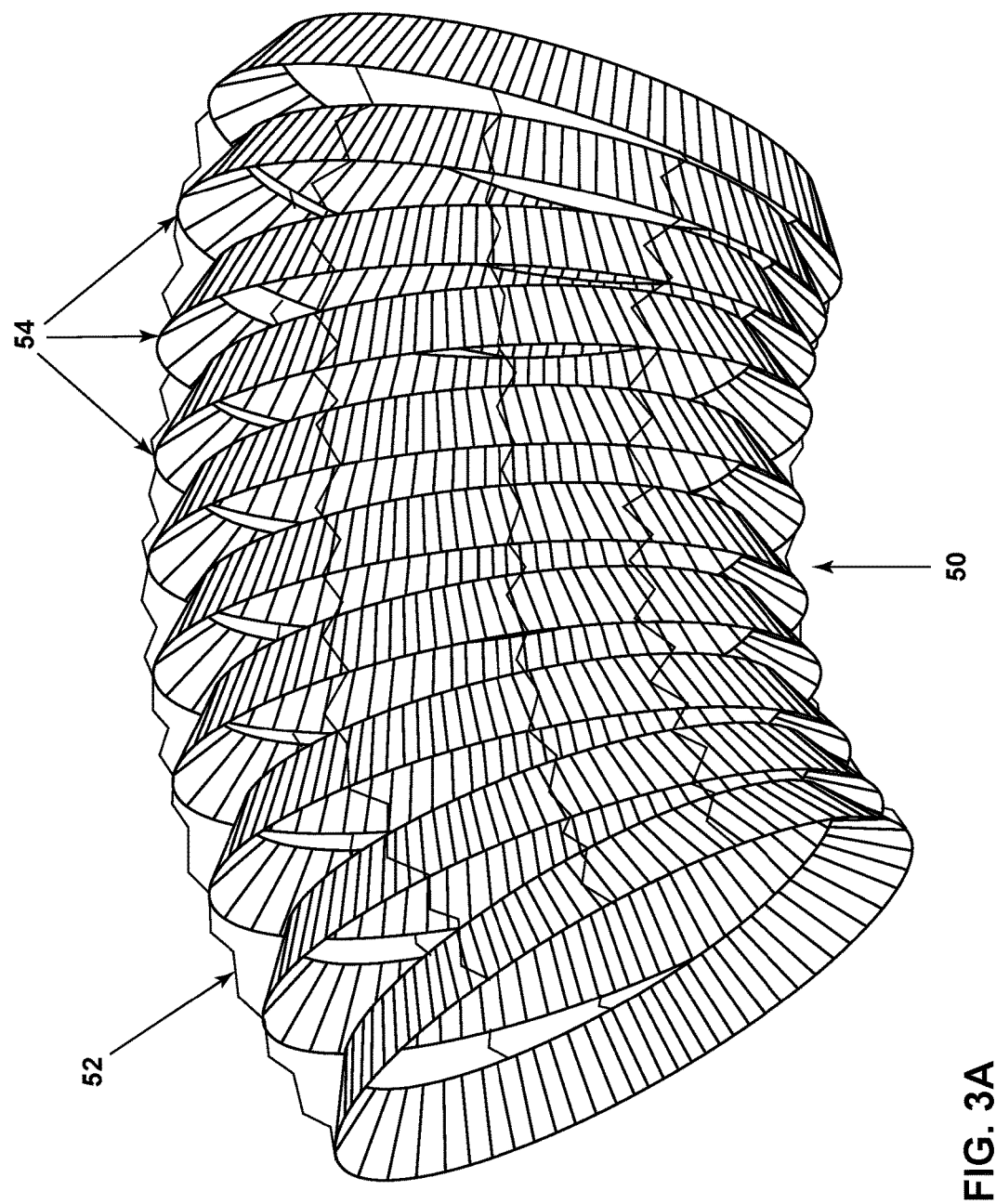
FIG. 3A is a perspective diagram illustrating another example embolic protection device.

FIG. 3A is a perspective diagram illustrating another example embolic protection device. As illustrated in FIG. 3A, embolic protection device 50 comprises a frame 52, and a plurality of flow-modulating elements 54 within and coupled to the frame 52. Flow-modulating elements 54 have a ring-like or generally annular profile. The configuration of flow-modulating elements 54 and frame 52 provides a longitudinal passageway through embolic protection device 50—generally along the longitudinal axis of embolic protection device 50. The construction and/or materials of frame 52 and flow-modulating elements 54 may be compressed and loaded onto a catheter-tip, allowing embolic protection device 50 to assume a relatively smaller profile, e.g., diameter, for delivery through the vasculature to a target vessel, e.g., the aortic arch, and to be expanded to engage the wall of the target vessel, e.g., the aortic arch.

The ring-shape platform upon which the deflective surfaces are based allows the device to be deployed in any radial orientation, and once deployed, allows relatively unobstructed transit of wires, catheters, and other intravascular instruments through the device without interfering with the function of the device. Also, the expansion of embolic protection device 50 to engage or very nearly engage the inner surface of the vessel, e.g., aorta, facilitates an open channel. The number of flow-modulating elements 54 depicted in FIG. 3A is merely an example. In some examples, embolic protection devices as described herein may include at least two flow-modulating elements, which may be positioned proximal to one or more branches of the vessel in which the device is implanted, e.g., proximal to the cranially-supplying arterial branches of the aortic arch.

As illustrated in FIG. 3A, embolic protection device 50 may comprise a series of embolic flow-modulating elements 54 maintained spaced-apart in formation along the longitudinal axis of embolic protection device 50 by an outer scaffolding, e.g., frame 52, which may be similar to a stent. Each of the embolic flow-modulating elements 54 is axially separated from the adjacent flow-modulating elements by an optimal distance determined by computational fluid dynamics of the target vessel and branch vessels, e.g., in the aorta and cranially-supplying vessels. The separation between the adjacent flow-modulating elements 54 allows open channels for blood flow to branch vessels, e.g., to the brain, while weighted embolic particles are more likely deflected or otherwise directed downstream to generally less clinically critical locations as compared to the brain.

Figure 3B:
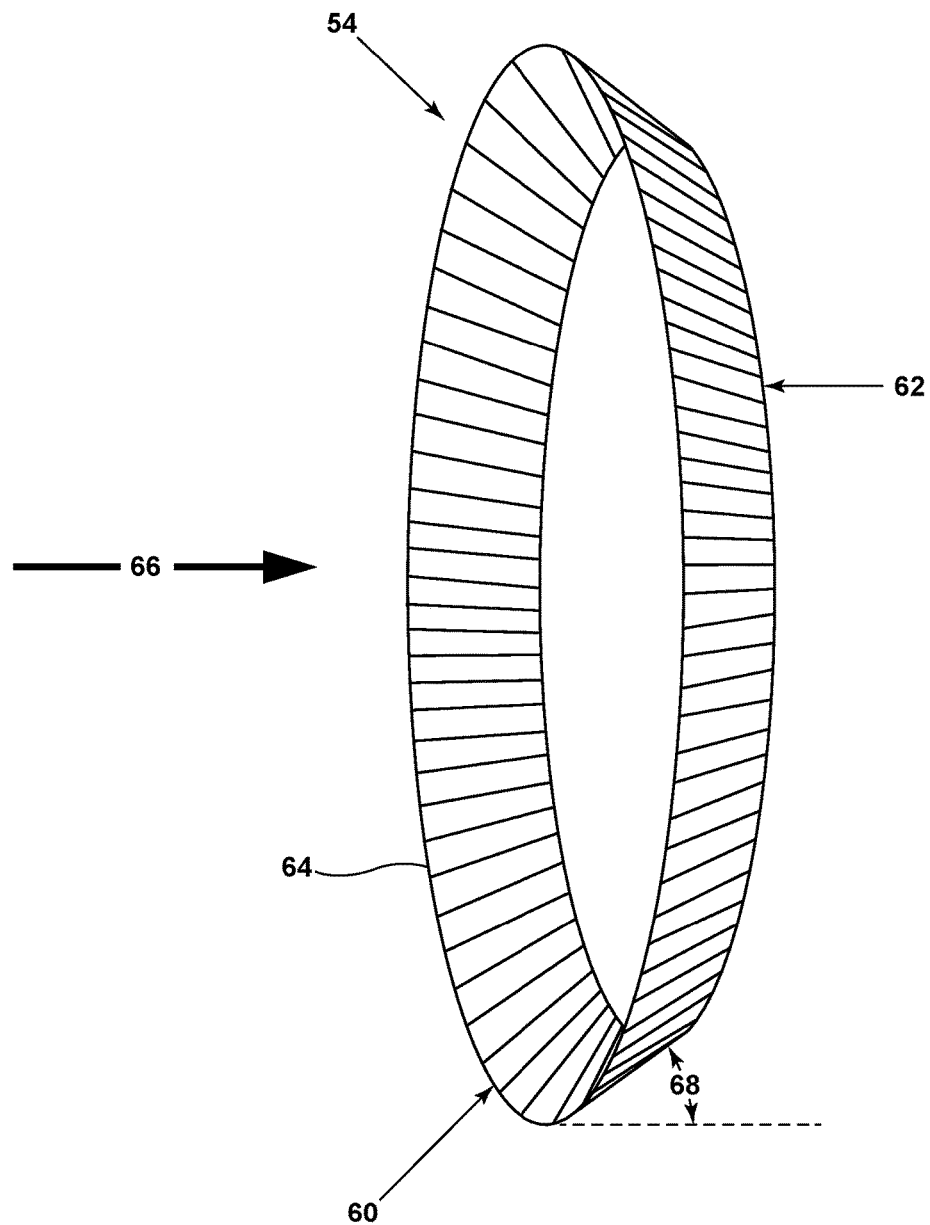
FIG. 3B is a perspective diagram further illustrating a flow-modulating element of the example embolic protection device of FIG. 3A.

FIG. 3B is a perspective diagram further illustrating a flow-modulating element 54 of embolic protection device 50 of FIG. 3A. As illustrated in FIG. 3B, flow-modulating element 54 comprises a first ring 60 with a first, relatively larger diameter, and a second ring 62, with a second, relatively smaller diameter. A deflective surface 64 is disposed between, e.g., bridges, the first ring 60 and the second ring 62. When flow-modulating element 54 is implanted within a vessel, e.g., the aortic arch, second ring 62 is more distally located relative to blood flow 66, e.g., more distally located within the aortic arch. Accordingly, deflective surface 64 faces primary blood flow 66. Based on the difference between the first and second diameters of the first ring 60 and the second ring 62, deflective surface 64 is oriented at an angle 68 with respect to the longitudinal axis of embolic protection device 50. Angle 68 may be between ten and eighty degrees, between 30 and 60 degrees, or a similar value that is otherwise deemed optimal per associated simulation and testing. As illustrated in FIG. 3B, flow-modulating element 54 may take the shape resembling a frustum of a cone.

Figure 4:
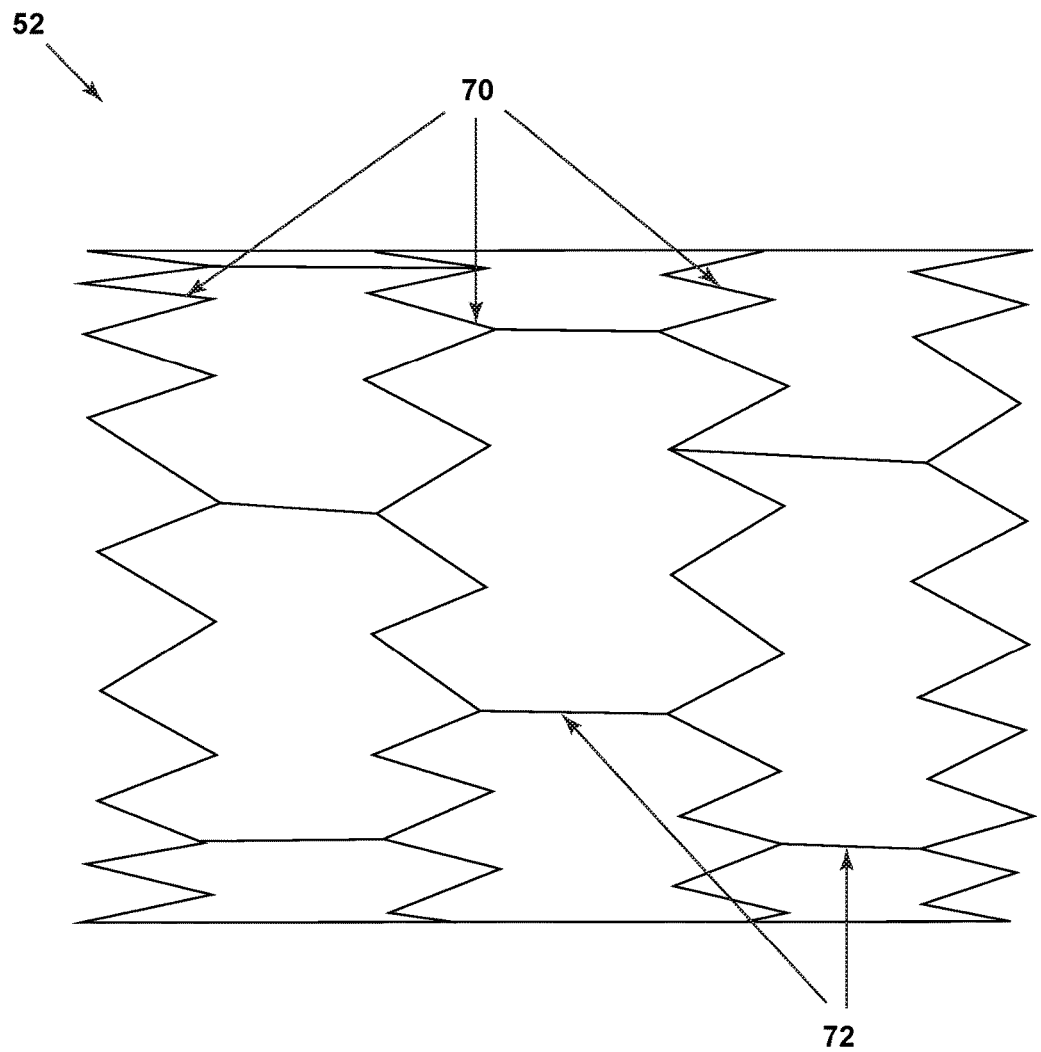
FIG. 4 is a conceptual diagram illustrating an example frame for an embolic protection device.
Figure 6:
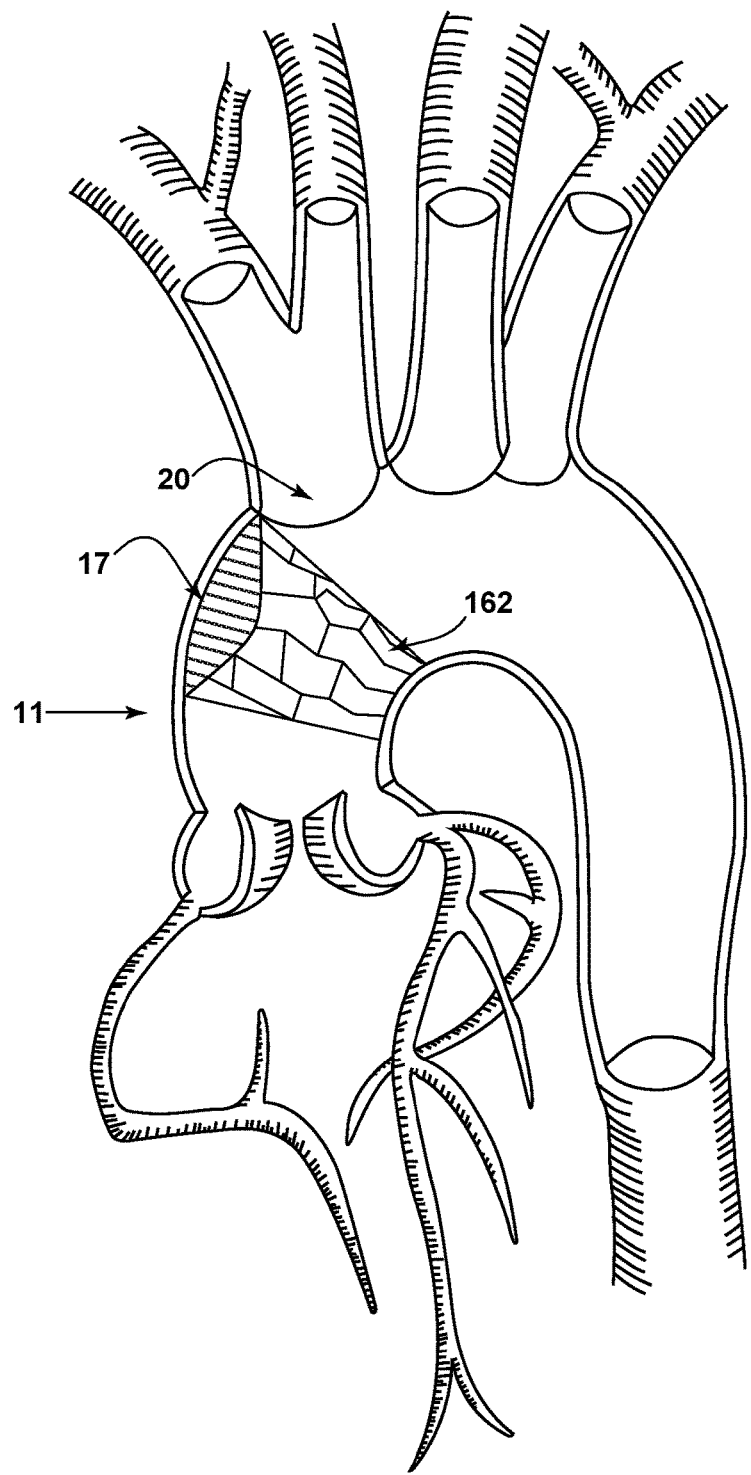
FIG. 6 is cross-sectional diagram illustrating another embolic protection device

FIG. 4 is a conceptual diagram illustrating an example configuration of frame 52 of embolic protection device 50 of FIG. 3A. Frame 52 is cylindrical, and may be largely fenestrated, as shown in FIG. 6. In general, frame 52 may comprise a plurality of linked elements configured to allow frame 52 to be compressed to a smaller profile, e.g., diameter, and to be expand to engage or nearly engage a vessel wall. In this manner, frame 52 may be constructed similar to a stent. In the illustrated example, frame 52 comprises a plurality of circumferential elements 70 that are circuitous and are linked by a plurality of struts 72 arranged along the longitudinal axis of the frame. In other examples, the longitudinal elements may be circuitous, or both the longitudinal and circumferential elements may be circuitous. In general, frame 52 may be constructed using any elements, techniques, or materials known for stents.

Embolic protection devices as described herein, e.g., one or both of frame 52 or flow-modulating elements 54, may be formed of nitinol and/or another composite or other material capable of collapse and memory shape re-assumption and retention. Deflective surfaces 64 may be comprised of the same material as the rings 60, 62 and/or frame 52, or any fabric or other material, including, but not limited to, polytetraflouroethylene (PTFE, Teflon®), expanded PTFE (GoreTex®), polyethylene (PE), polyethylene terephthalate (PETE), or some other polymer. Embolic protection devices, and particularly deflective surfaces 64, could be formed of or coated with bovine, porcine, ovine, or other species-derived pericardium. Depending on the construction and materials of deflective surfaces 64, e.g., if mesh-like, the deflective surfaces may act initially as a filter and/or flow modulator, and then transition to flow-modulating-only, depending on the degree of endothelialization of the deflective surfaces.

Figure 5A:
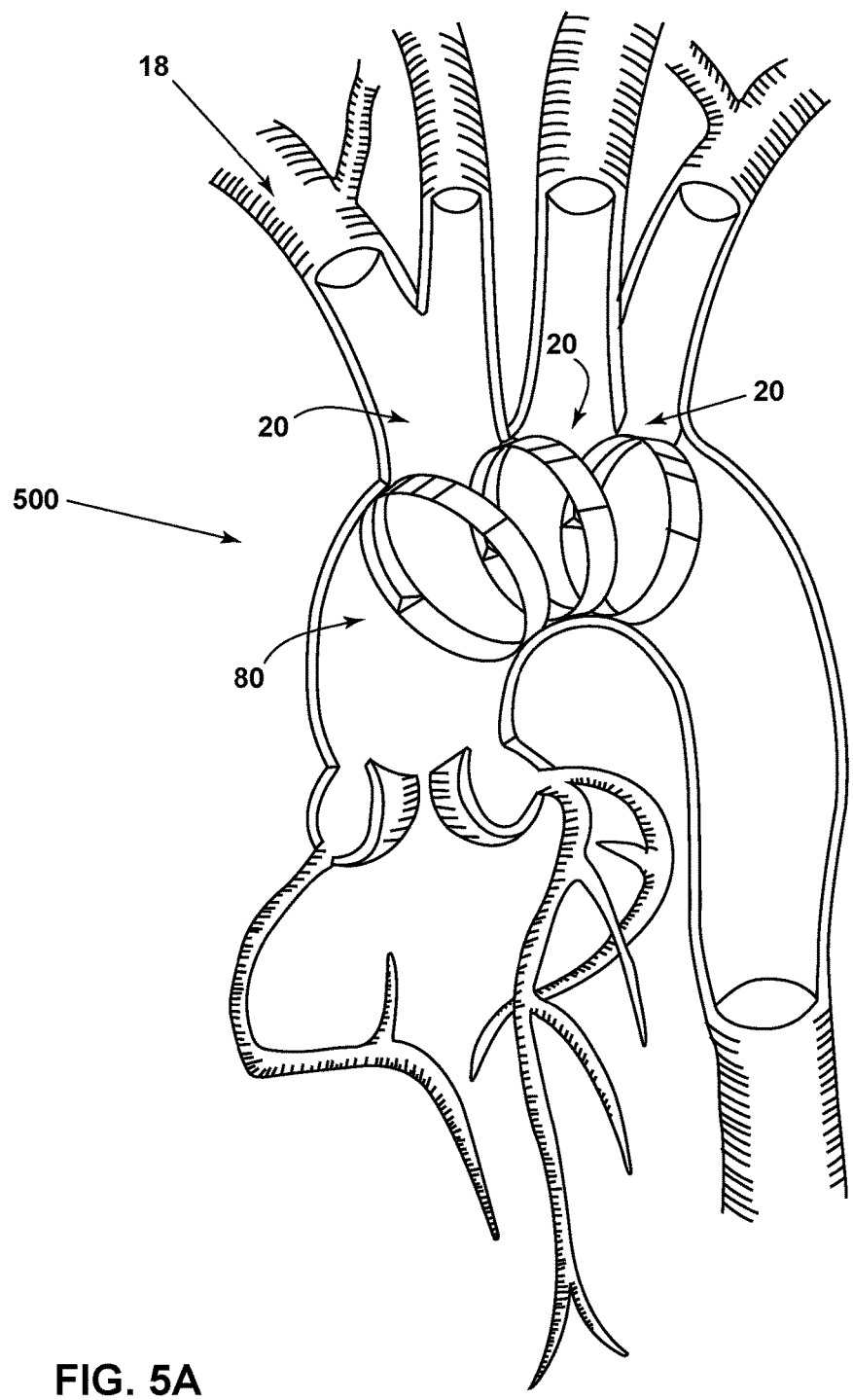
FIG. 5A is a conceptual diagram illustrating another example embolic protection device.

FIG. 5A is conceptual diagram illustrating another example embolic protection device 500. As shown in FIG. 5A, embolic protection device 500 includes a plurality of flow-modulating elements 80. In the example shown, embolic protection device 500 includes 3 flow-modulating elements 80. However, embolic protection device 500 may have more or less flow-modulating elements 80. As illustrated in FIG. 5A, each of the flow-modulating elements 5A is position proximal to an ostium 20. Each ostia 20 leads to a branch vessel 18. The flow-modulating elements divert the flow of emboli away from ostia 20, thereby preventing the occurrence of a stroke. In addition, as shown, flow-modulating elements 80 are radially asymmetrical.

Figure 5B:
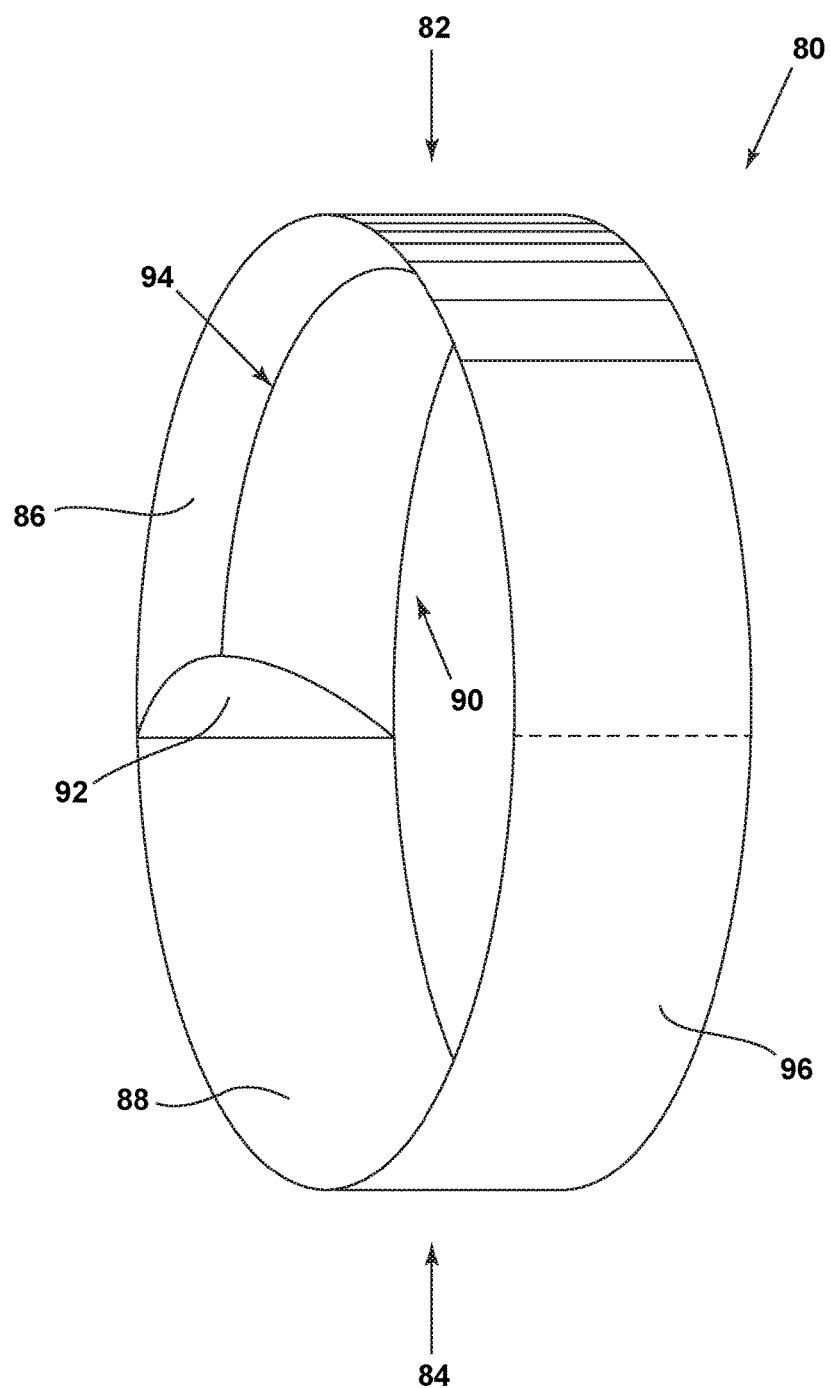
FIG. 5B is a perspective diagram illustrating an example flow-modulating element for the embolic protection device of FIG. 5A.
Figure 5C:
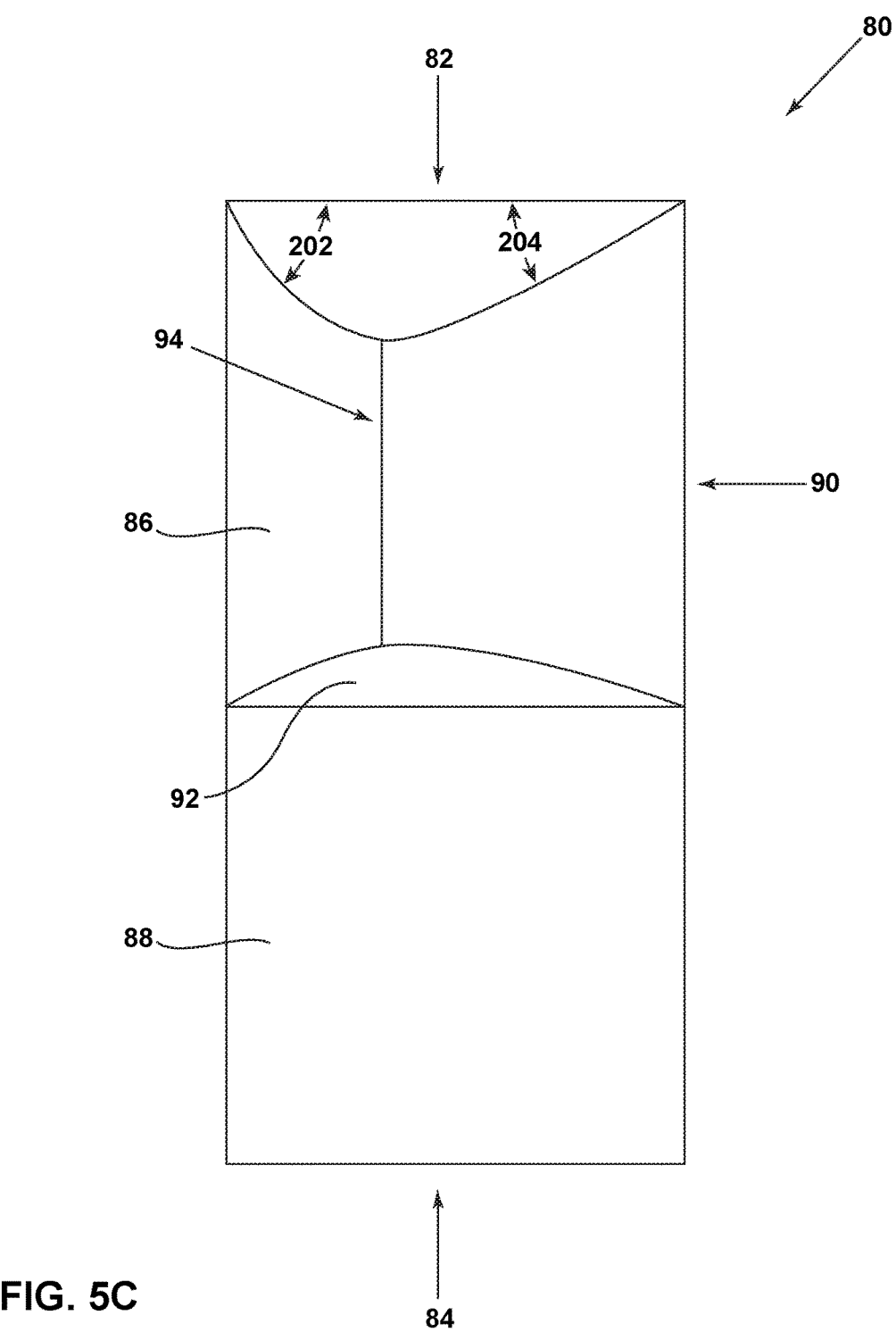
FIG. 5C is a cross-sectional diagram further illustrating the example flow-modulating element of FIGS. 5A and 5B.

FIG. 5B is a perspective diagram illustrating another example flow-modulating element 80 for an embolic protection device. FIG. 5C is a cross-sectional diagram further illustrating flow-modulating element 80 of FIGS. 5A and 5B. Flow-modulating element 80 is an example of a radially-asymmetric flow-modulating element. A plurality of flow-modulating elements 80 may be axially spaced within a frame to form a radially-asymmetric embolic protection device as shown in FIG. 5A. In some examples, an embolic protection device may comprise a single flow-modulating element 80.

Flow-modulating element 80 has a first portion 82, which may be positioned superiorly along the greater aortic arch 24 when implanted in the aortic arch 12. Flow-modulating element 80 also comprises a second portion 84, which may be positioned inferiorly along the lesser aortic arch 26 when implanted in the aortic arch 12. First portion 82 comprises a deflective surface 86, while second portion 84 comprises a relatively flat surface 88. Although in the illustrated example approximately half of the circumference of flow-modulating element 80 includes deflective surface 86, in other examples a greater or lesser portion of the circumference may comprise a deflective surface. Furthermore, in some examples, non-contiguous portions of the circumference may comprise deflective surfaces.

Deflective surface 86 faces the primary flow of blood. A trailing surface 90 faces away from the flow of blood. Deflective surface 86, trailing surface 90, and surface 92 meet at a peak 94, the entirety of which resembles a hydrofoil shape, as illustrated in 7B, for example. The angles of deflective surface 86 and trailing surface 90 may be chosen based on a desired hydrofoil shape. In addition, in some examples, deflective surface 86 is relatively smaller than trailing surface 90, resulting in peak 94 being positioned towards the front of flow-modulating element 80 with respect to blood flow. This placement may result in less turbulence along the trailing surface 90. In the illustrated example, an outer surface 96 of deflective element 80 is generally annular, in contrast to the frustum shape of the outer surface of flow-modulating element 54 illustrated in FIG. 3B. The generally annular shape of outer surface 96 may be selected for reasons of manufacturability, in some cases. In some examples, outer surface 96 may be blood permeable. In some examples, outer surface 96 may be fenestrated. For example, outer surface 96 may be made up of struts and circumferential elements as illustrated in FIG. 4.

Deflective surface 86 and trailing surface 90 may be oriented at respective angles, 202 and 204, with respect to the longitudinal axis of the embolic protection device. The angles may be the same, or different. In the illustrated example, the angle 202 of deflective surface 86 is greater than angle 204 of trailing surface 90. The angled trailing surface 90, and relative angles of deflective surface 86 and trailing surface 90, may affect the flow of blood through the center of flow-modulating element 80, and through a longitudinal passageway of an embolic protection device including flow-modulating elements 80. The blood flow, as affected by flow-modulating elements 80, may cause emboli to preferentially travel through the center or inferior portions of the longitudinal passageway, avoiding superiorly-located arterial branches, e.g., ostia 20 of branches 18 (FIGS. 1A and 1B).

In some examples, deflective surface 86 and trailing surface 90 may form a hydrofoil shaped flow-modulating element. The hydrofoil-shaped flow-modulating element may be configured to limit or avoid additional turbulence. A smooth hydrofoil-shaped flow-modulating element may also maintain the integrity of laminar flow at the outer curvature of the vessel. Minimizing additional turbulence is desirable, particularly for flow-modulating elements implanted for long periods of time for stroke prophylaxis. In particular, additional turbulence within the aortic arch may lead to additional embolic complications.

FIG. 6 is a perspective diagram illustrating another example embolic protection device 200. Embolic protection device 200 includes a flow-modulating element 160 and a frame 162. Flow-modulating element 160 is positioned along inner wall 14 of greater aortic arch 24. Embolic protection device 200 may be positioned so that flow-modulating element 160 is proximal to the first cranially-directed arterial ostium 20 after aortic valve 36, i.e., between the aortic valve 36 and the arterial ostia 20 most proximal to aortic valve 36 or, in other words, more proximal relative to the aortic value than the arterial ostia most proximal to the aortic valve. Frame 162 may be substantially similar to frame 52 as illustrated in FIG. 4. In some examples, embolic protection device 200 may be substantially similar to flow-modulating element 80 discussed above with respect to FIGS. 5A, 5B, and 5C. For example, flow-modulating element 160 may have a hydrofoil like shape similar to that of flow-modulating element 80.

FIG. 7A is a conceptual diagram illustrating blood flow in an aortic arch 12. According to Bernoulli's principle, as laminar fluid flow 23 approaches a curve, velocity at the greater or outer curvature (concavity) 24 (FIG. 1A) is slower, while velocity at the lesser or inner curvature (convexity) 26 (FIG. 1A) is faster. Slower velocity is accompanied by higher pressure, while faster velocity is accompanied by lower pressure. Additionally, slower velocity is accompanied by relatively more laminar flow (relatively lower Reynolds number), while faster velocity is accompanied by more turbulent flow 25 (relatively higher Reynolds number). In order to minimize turbulent flow, in some examples, flow-modulating elements are placed asymmetrically around the aortic arch, so that flow-modulating elements encounter laminar flow 23, and not the already turbulent flow 25 near the inner curvature of the aortic arch.

Figure 7B:
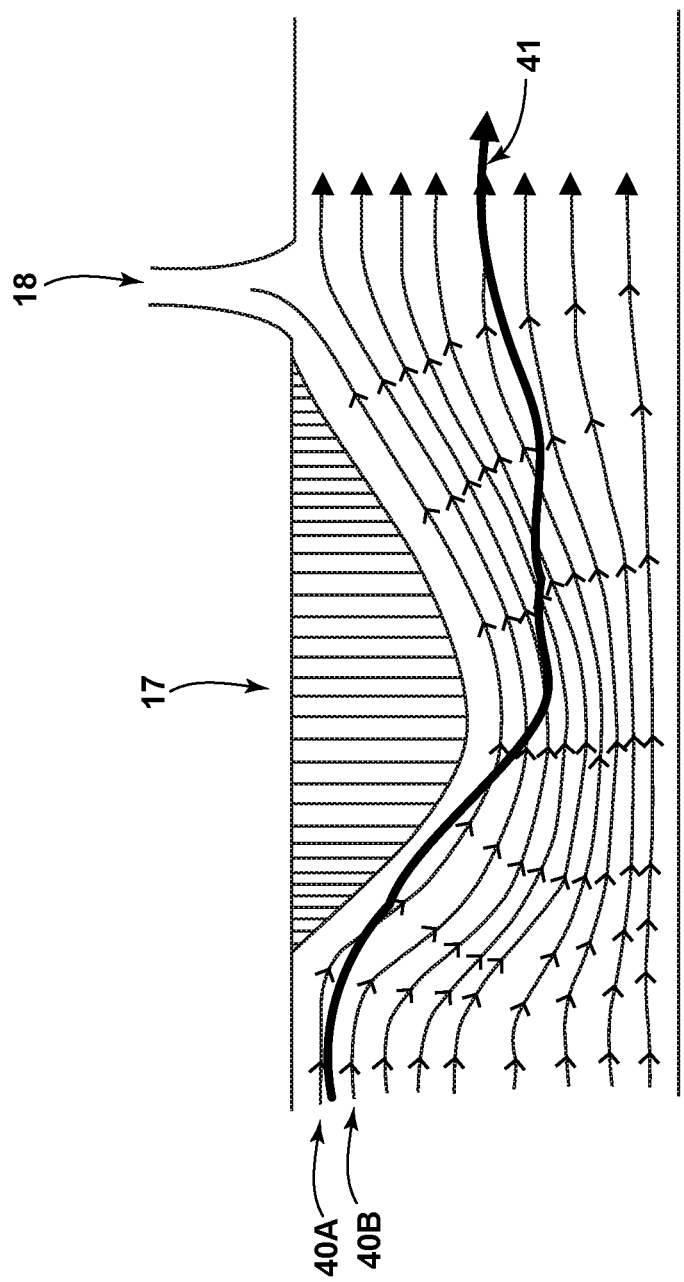
FIG. 7B is a conceptual diagram illustrating blood flow and particle trajectory around a flow-modulating element.

FIG. 7B is a conceptual diagram illustrating blood flow and particle trajectory around a flow-modulating element. The flow-modulating element 17 of FIG. 7B includes a leading (deflective) surface and a trailing surface with relative angles. More particularly, the flow-modulating element of FIG. 7B has a hydrofoil-like shape. Ideally, fluid would flow in a laminar pattern as shown, presuming the hydrofoil's angle of attack does not exceed the threshold beyond which vortices will form and create turbulence and drag. A solid particle of different size/density traveling towards the same surface will be deflected and, due to the hydrofoil shape, assume a new trajectory assisted by an adjacent streamline, thus avoiding the branch vessel, as illustrated in FIG. 7B. In some examples, the deflection of the particle occurs without the particle coming in contact with the leading surface of the flow-modulating element. The flow-modulating element interrupts the fluid flow, causing the fluid streamlines to converge as they approach the deflective surface and diverge along the trailing surface. The solid particle may shift into an adjacent streamline. As shown in FIG. 7B, the trajectory 41 of a solid particle shifts from a first streamline 40A to a second, adjacent, streamline 40B. The shift in streamline results in the particle avoiding branch vessel 18.

Figure 7C:
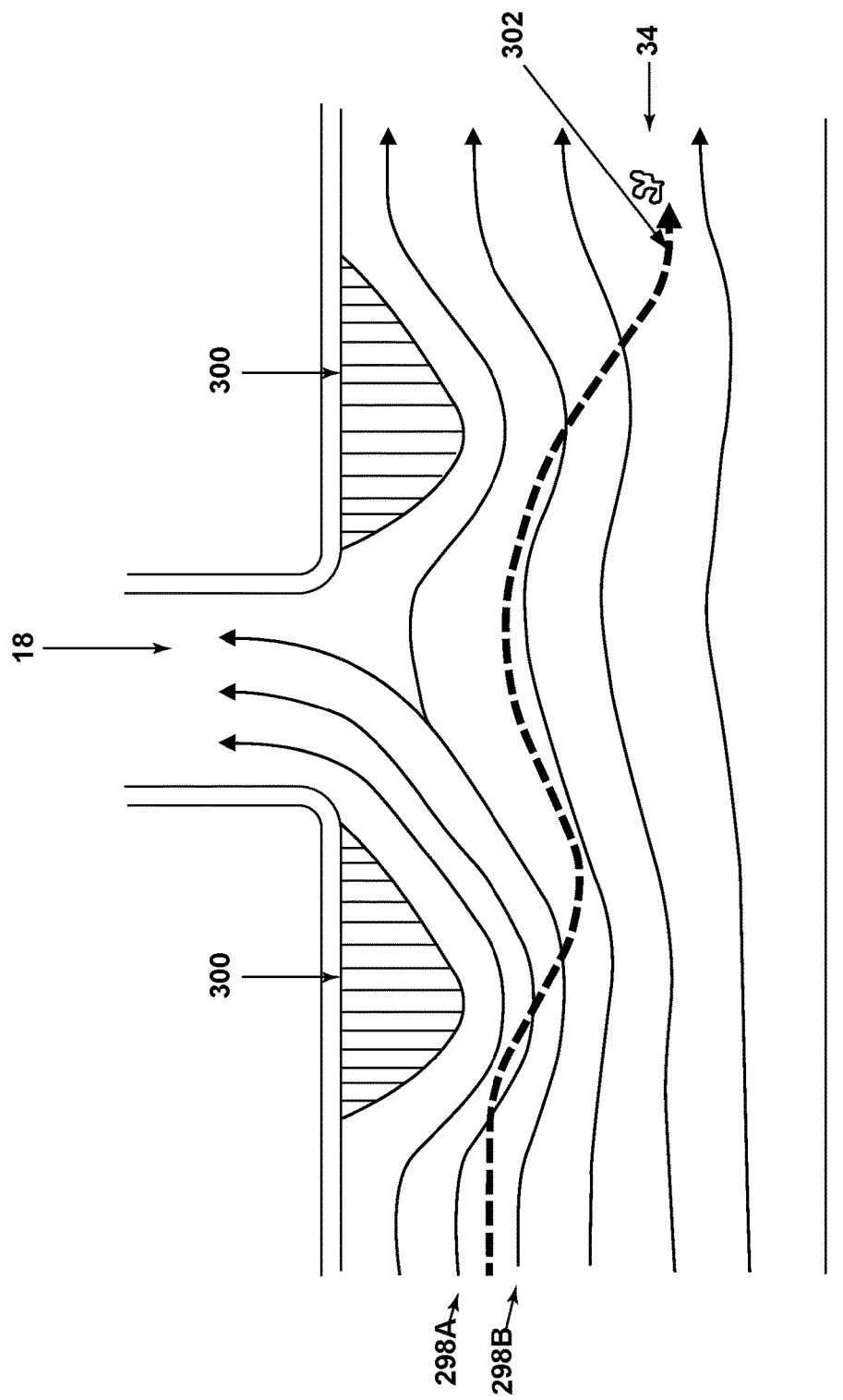
FIG. 7C is a conceptual diagram illustrating blood flow and particle trajectory around a plurality of flow-modulating elements.

FIG. 7C is a conceptual diagram illustrating blood flow and particle trajectory around a plurality of flow-modulating elements. The flow-modulating elements 300 include a leading surface and a trailing surface with relative angles. The trajectory 302 of a solid particle 34 may start in a first streamline 298A and upon approaching each of the plurality of flow-modulating elements, shift direction. In some examples, particle 34 may shift from a first streamline 298A to a second streamline 298B that is farther away from the plurality of flow-modulating elements 300. In some examples, trajectory 302 may follow the modulation of a particular streamline.

Figure 7D:
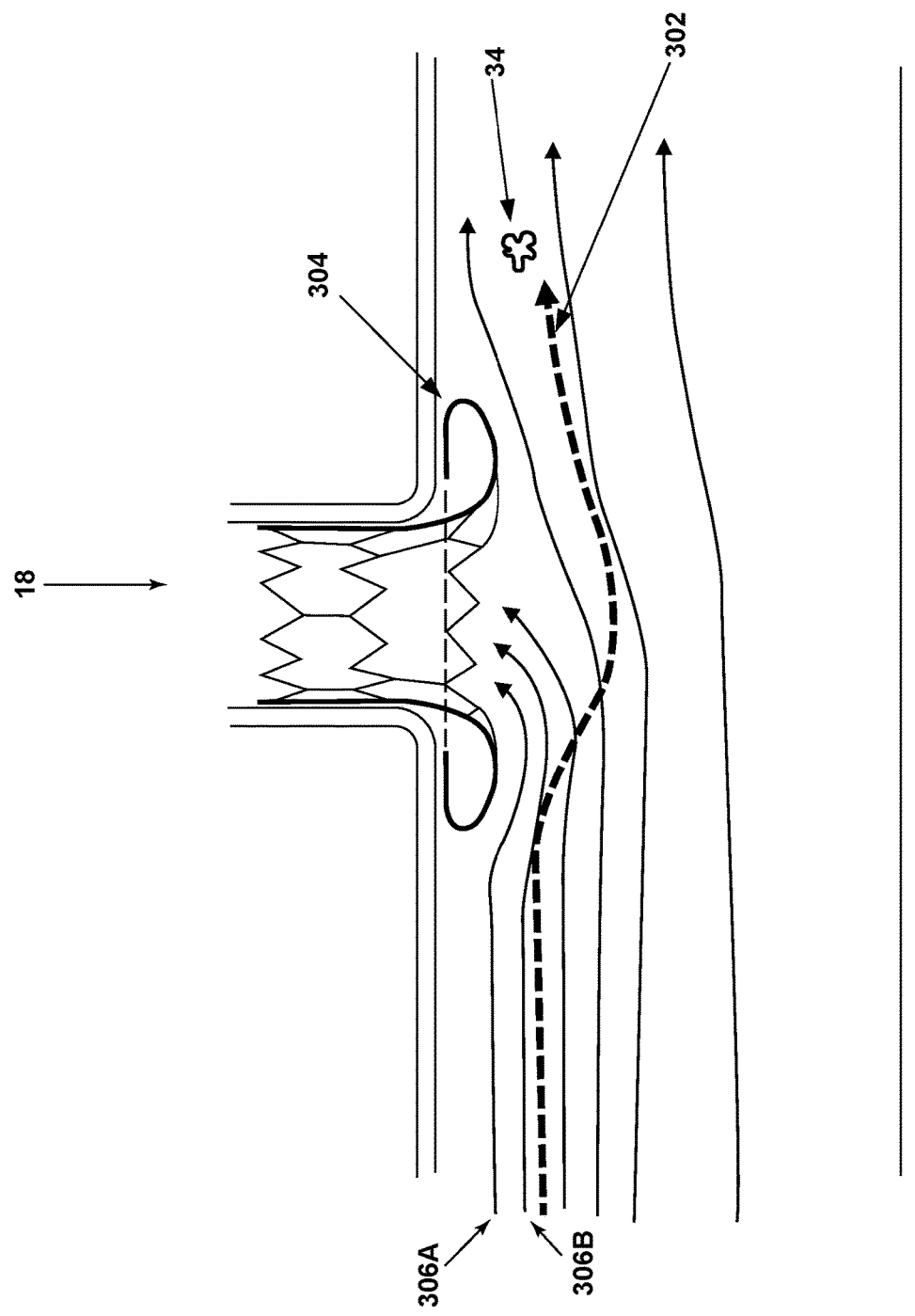
FIG. 7D is a conceptual diagram illustrating blood flow and particle trajectory around another example embolic protection device.

FIG. 7D is a conceptual diagram illustrating blood flow and particle trajectory around another example embolic protection device. Flow-modulating element 304 deflects streamline 306. In addition, particle trajectory shifts from a first streamline 306A to a second streamline 306B as blood flow comes in contact with flow-modulating element 304.

FIG. 8 is a conceptual diagram illustrating another example embolic protection device 100 implanted within a blood vessel 102. Embolic protection device 100 includes superior flow-modulating elements 104A and inferior flow-modulating elements 104B (collectively, "flow-modulating elements 104"). Flow-modulating elements 104 include deflective surfaces 106 that face blood flow 108 through the vessel 102. Embolic protection device 100 engages, or nearly engages, the inner wall of vessel 102, and is positioned such that flow-modulating elements 104 are proximal to branch vessel 110. As illustrated in FIG. 8, an embolus 112 may be deflected off of a deflective surface 106, and thereafter follow a trajectory with blood flow 108 through the longitudinal passageway of embolic protection device 100 that avoids branch vessel 110.

FIG. 9 is a conceptual diagram illustrating another example embolic protection device 120 implanted within blood vessel 102. While embolic protection device 100 may be symmetric, e.g., radially symmetric, in that it includes both superior and inferior flow-modulating elements 106, embolic protection device 120 may be asymmetric, e.g., radially asymmetric. In particular, embolic protection device 120 includes flow-modulating elements 104A on the superior (cranial) portion of the device. However, an inferior portion of the device includes a relatively flat inner surface 122, or longitudinal passageway wall.

In some examples, embolic protection devices, e.g., embolic protection devices 100, 120, may appear on a macroscopic level to be similar to a standard stent structure. However, rather than a flat low profile scaffolding structure on both the luminal and vessel-opposing surfaces, there are tilted or angled flow-modulating elements formed on the inner or luminal side of the stent structure, providing a deflective surface or series of deflective surfaces.

Figure 10:
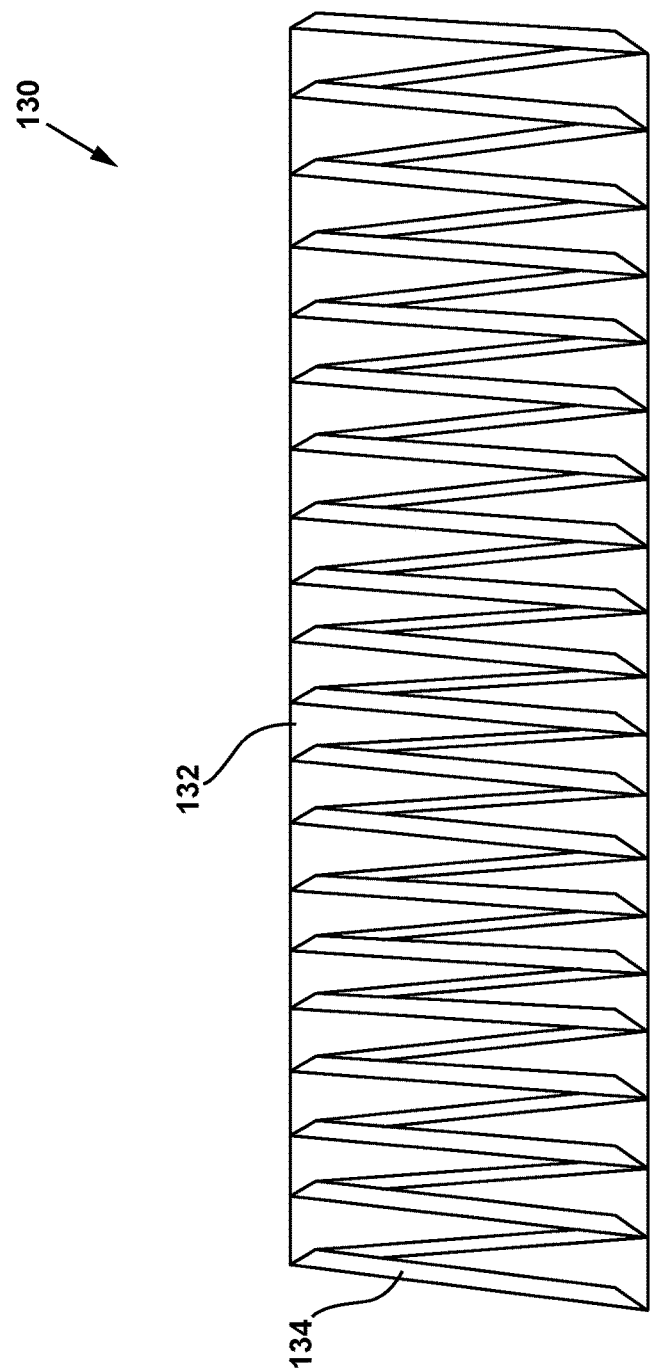
FIG. 10 is a conceptual diagram illustrating another example embolic protection device.

FIG. 10 is a conceptual diagram illustrating another example embolic protection device 130. Embolic protection device 130 includes a frame 132, which may be similar to or the same as frame 52 (FIG. 4). Embolic protection device 130 further includes an embolic flow-modulating element 134 within and coupled to frame 132.

Embolic flow-modulating element 134 is helical. More particularly, embolic flow-modulating element 134 may include an outer helix structure with a first diameter, and an inner helix structure with a second, smaller diameter. A deflective surface may be formed between or otherwise span the helix structures. The outer helix structure may be coupled to frame 132. The diameter of the inner helix structure may define, and may be selected to provide, a longitudinal passageway through embolic protection device 130, which may be sufficient for passage of various procedure instruments.

Figure 11:
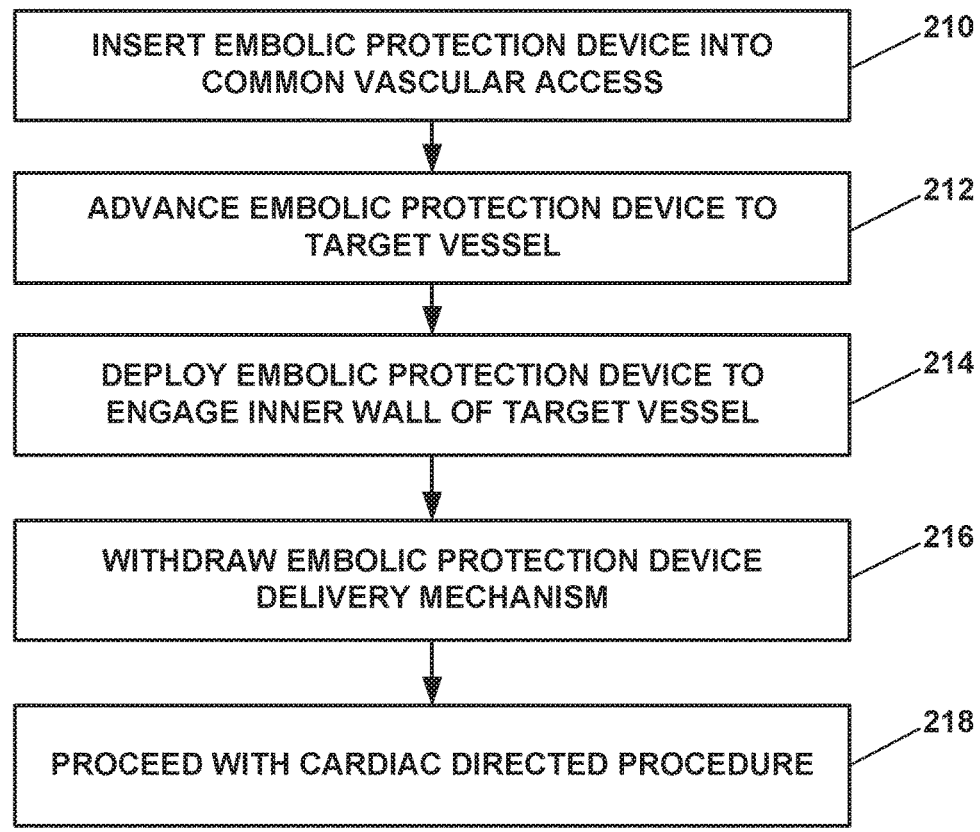
FIG. 11 is a flow diagram illustrating an example method of implanting an embolic protection device and performing a cardiac procedure.

FIG. 11 is a flow diagram illustrating an example method for implanting an embolic protection device to prior to or during any left-sided or systemic circulation cardiac procedure. As discussed below with respect to FIGS. 12 and 13, in various examples, a clinician inserts an embolic protection device as described herein into a common vascular access point (210). The clinician may then advance the embolic protection device to a target vessel, such as the aortic arch (212). In other examples, the embolic protection device may be advanced to one of the branch vessels. The embolic protection device may be delivered using a catheter or other catheter-based delivery mechanism.

The clinician may then deploy the embolic protection device, e.g., to engage the inner wall of the aortic arch or other target vessel (214). The embolic protection device may be self-expanding, e.g., may expand upon release from the delivery mechanism. Embodiments in which the embolic protection device comprises nitinol may be capable of self-expansion. In some examples, the embolic protection device may be expanded by balloon or other expandable element of the delivery mechanism. In some examples, the embolic protection device may be radiopaque or include radiopaque elements to facilitate visualization during implantation. Visualization may be of particular importance in the case of asymmetric embolic protection devices, for which orientation of flow-modulating elements and deflective surfaces proximal to branch vessels is desired. In some examples, the clinician may position the embolic protection device so that the flow-modulating element is located prior to the first ostia 20 on the greater curvature 24. In other examples, the clinician may position the embolic protection device so that a portion of the embolic protection device is placed within a branch vessel, while the flow-modulating element encircles the ostium of the branch vessel and extends partially into the lumen of the aortic arch. After the embolic protection device is implanted, the clinician may withdraw the embolic protection device delivery mechanism, e.g., through the common access (216). After the clinician has withdrawn the embolic protection device delivery system, the clinician may proceed with a cardiac directed procedure (218). The embolic protection device may remain in place while the valvuloplasty, TAVR, endocardial ablation, or other cardiac procedure is performed. The use of an embolic protection device may be indicated for various cardiac procedures with a relatively high stroke risk. After the cardiac procedure is completed, the embolic protection device may be removed. In other examples, the embolic protection device may remain in place for a period of time after the cardiac procedure is concluded.

Figure 12:
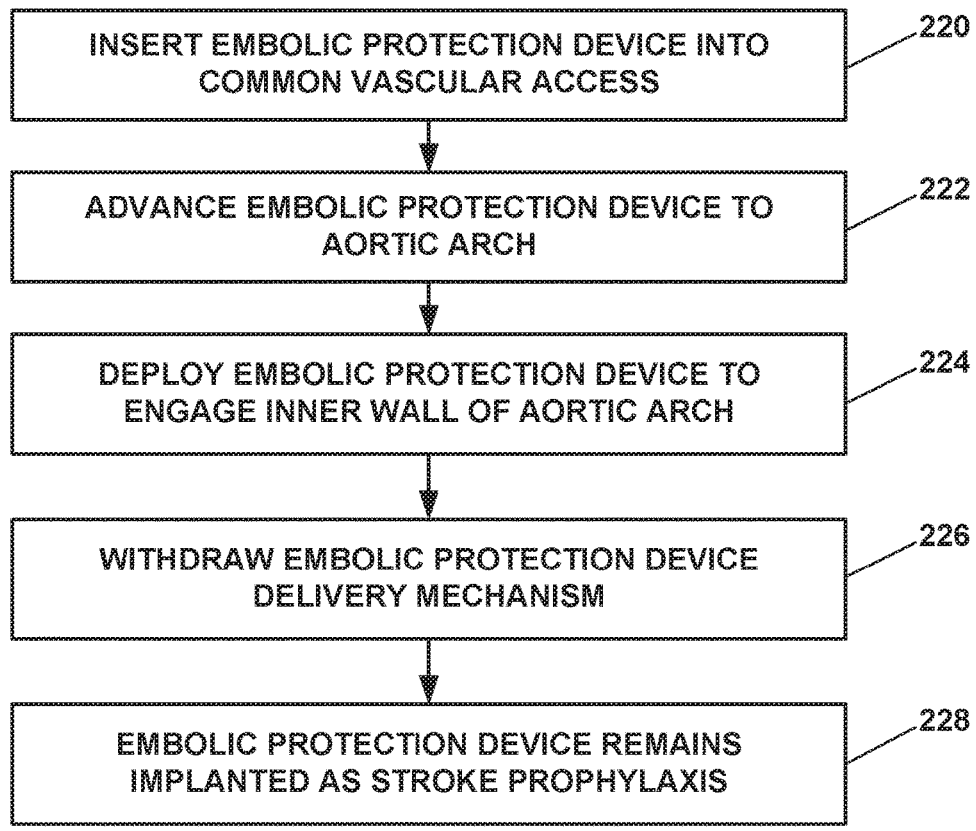
FIG. 12 is a flow diagram illustrating an example method of implanting an embolic protection device for stroke prophylaxis.

FIG. 12 is a flow diagram illustrating an example method for implanting an embolic protection device to provide stroke prophylaxis. In some examples, an embolic protection device may be implanted in a patient based on an increased likelihood of stroke. The use of the embolic protection device may be indicated when a patient is deemed high-risk for use of other stroke prevention techniques, namely anticoagulation therapy. As discussed above with respect to FIG. 11, in various examples, a clinician inserts an embolic protection device as described herein into a common vascular access point (220). The clinician may then advance the embolic protection device to a target vessel, such as the aortic arch (222). The embolic protection device may be delivered using a catheter or other catheter-based delivery mechanism.

The clinician may then deploy the embolic protection device, e.g., to engage the inner wall of the aortic arch or other target vessel (224). The embolic protection device may be self-expanding, e.g., may expand upon release from the delivery mechanism. Embodiments in which the embolic protection device comprises nitinol may be capable of self-expansion. In some examples, the embolic protection device may be expanded by balloon or other expandable element of the delivery mechanism. In some examples, the embolic protection device may be radiopaque or include radiopaque elements to facilitate visualization during implantation. Visualization may be of particular importance in the case of asymmetric embolic protection devices, for which orientation of flow-modulating elements and deflective surfaces proximal to branch vessels is desired. In some examples, the clinician may position the embolic protection device so that the flow-modulating element is located prior to the first ostia 20 on the greater curvature 24. After the embolic protection device is implanted, the clinician may withdraw the embolic protection device delivery mechanism, e.g., through the common access (226). The clinician may leave the embolic protection device implanted in the patient in order to provide stroke prophylaxis (228). In some examples, a frame of the embolic protection device may be made of a porous material that allows endothelialization and enhanced anchoring of the device.

Figure 13:
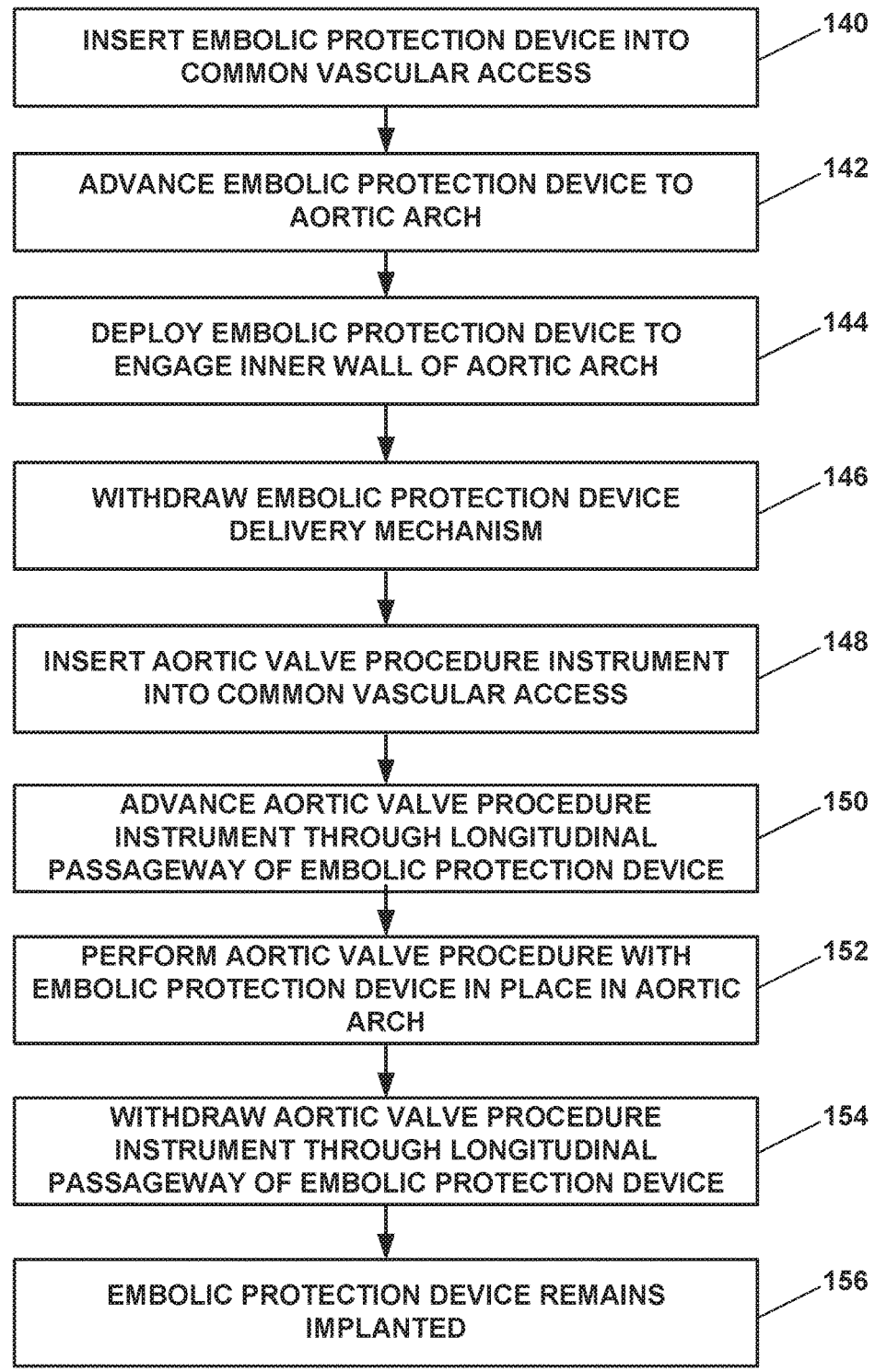
FIG. 13 is a flow diagram illustrating an example method for implanting an embolic protection device and performing an aortic valve procedure.

FIG. 13 is a flow diagram illustrating an example method for implanting an embolic protection device and performing an aortic valve procedure. According to the example method, a clinician inserts an embolic protection device as described herein into a common vascular access point (140). The clinician may then advance the embolic protection device to a target vessel, such as the aortic arch (142). The embolic protection device may be delivered using a catheter or other catheter-based delivery mechanism.

The clinician may then deploy the embolic protection device, e.g., to engage the inner wall of the aortic arch or other target vessel (144). The embolic protection device may be self-expanding, e.g., may expand upon release from the delivery mechanism. Embodiments in which the embolic protection device comprises nitinol may be capable of self-expansion. In some examples, the embolic protection device may be expanded by balloon or other expandable element of the delivery mechanism. In some examples, the embolic protection device may be radiopaque or include radiopaque elements to facilitate visualization during implantation. Visualization may be of particular importance in the case of asymmetric embolic protection devices, for which orientation of flow-modulating elements and deflective surfaces proximal to branch vessels is desired. In some examples, the clinician may position the embolic protection device so that the flow-modulating element is located prior to the first ostium 20 on the outer arch 24 with respect to aortic valve 36. After the embolic protection device is implanted, the clinician may withdraw the embolic protection device delivery mechanism, e.g., through the common access (146).

The clinician may then insert a procedure instrument, e.g., for valvuloplasty or TAVR, into the common vascular access (148), and advance the procedure instrument through the longitudinal passageway of the embolic protection device (150). The clinician may then perform the aortic valve procedure with the embolic protection device in place in the aortic arch (152). In some examples, the procedure preformed by the clinician may be another procedure requiring access through the aortic arch, such as a left-sided endocardial ablation. When the procedure is completed, the clinician may withdraw the aortic valve procedure instrument through the longitudinal passageway of the embolic protection device (154). The common vascular access may be closed, and the embolic protection device may remain implanted, e.g., chronically (156).

The embolic protection device may be implanted percutaneously via peripheral vessels or surgically via trans-apical or trans-aortic approach via catheter in the aortic arch, spanning the ostia of the cranially-supplying arterial branches. If ex-plantation becomes necessary, the embolic protection device may be retrieved via catheter or other means.

Figure 14A:
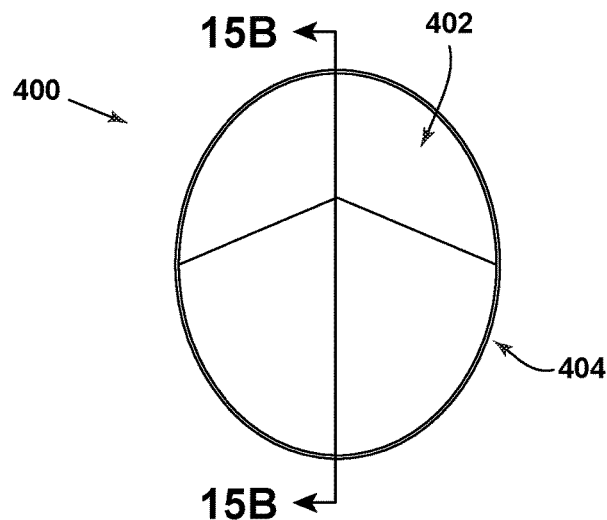
FIG. 14A is a conceptual diagram of a cross-sectional view of an example embolic protection device.

FIG. 14A is a conceptual diagram of a top view of an example embolic protection device 400. Embolic protection device 400 includes a flow-modulating element 402 and a frame 404. As shown, flow-modulating element 402 covers approximately half of the circumference of frame 404. When implanted the flow-modulating element 402 may be positioned so that it is located along the greater curvature of the vessel in which it has been implanted.

Figure 14B:
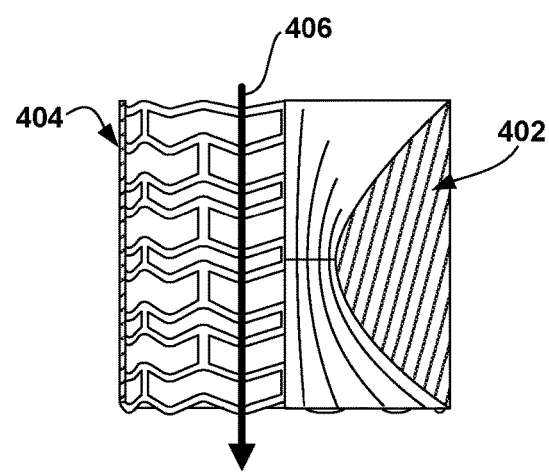
FIG. 14B is conceptual diagram of an orthogonal view of the embolic protection device of FIG. 14A.

FIG. 14B is conceptual diagram of an orthogonal cross-sectional view, taken along line 15B in FIG. 14A, of the embolic protection device 400 of FIG. 14A. As shown in FIG. 14B, the longitudinal axis 406 of embolic protection device 400 is open. When implanted in a vessel, flow-modulating element 402 has a hydrofoil shape facing the predominant flow of blood along the longitudinal axis 406.

Figure 14C:
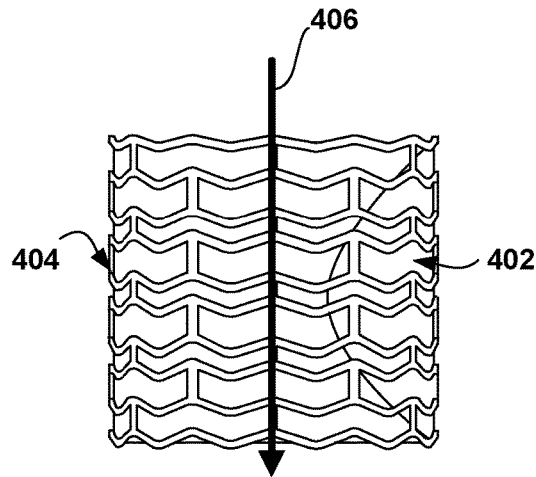
FIG. 14C is a conceptual diagram of a side view of the embolic protection device of FIGS. 14A and 14B.

FIG. 14C is a conceptual diagram of a side view of the embolic protection device of FIGS. 14A and 14B. Embolic protection device 400 includes flow-modulating element 402 and frame 404. Frame 404 may be comprised of circumferential portions and struts. In some examples, the composition of frame 404 may allow for expansion of frame 404 once it has been delivered to a target vessel.

Figure 15:
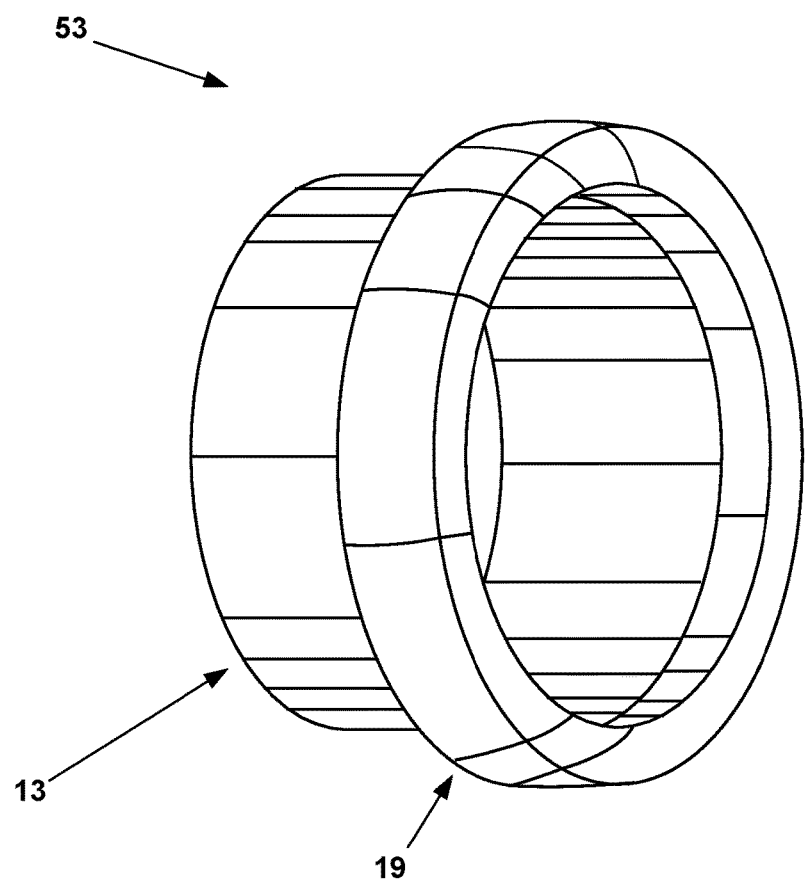
FIG. 15 is a conceptual diagram of an embolic portection device.

FIG. 15 is a conceptual diagram of another example embolic protection device 13. Embolic protection device 13 comprises a flow-modulating element 19 and a frame 53. Frame 53 is substantially cylindrical and may be largely fenestrated. In general, frame 53 may comprise a plurality of linked elements configured to allow frame 53 to be compressed to a smaller profile, e.g., diameter, and to be expand to engage or nearly engage a vessel wall. In this manner, frame 53 may be constructed similar to a stent. In the illustrated example, frame 53 comprises a plurality of circumferential elements that are circuitous and are linked by a plurality of struts arranged along the longitudinal axis of the frame. In other examples, the longitudinal elements may be circuitous, or both the longitudinal and circumferential elements may be circuitous. In general, frame 53 may be constructed using any elements, techniques, or materials known for stents.

In addition, flow-modulating element 19 may be attached to one end of the frame 53. In some examples, element 19 may be made of the same material as frame 53. Embolic protection devices as described herein, e.g., one or both of frame 53 or flow-modulating element 19, may be formed of nitinol and/or another composite or other material capable of collapse and memory shape re-assumption or retention. Deflective surfaces of the flow-modulating element may be comprised of the same material, or any fabric or other material, including, but not limited to, polytetraflouroethylene (PTFE, Teflon®), expanded PTFE (GoreTex®), polyethylene (PE), polyethylene terephthalate (PETE), or some other polymer. Embolic protection devices, and particularly deflective surfaces such as that of flow-modulating element 19, could be formed of or coated with bovine, porcine, ovine, or other species-derived pericardium. Depending on the construction and materials of deflective surface, e.g., if mesh-like, the deflective surfaces may act initially as a filter and/or flow modulator, and then transition to flow-modulating-only, depending on the degree of endothelialization of the deflective surfaces.

Various examples have been described. However, one of ordinary skill in the art will appreciate that various modifications may be made to the described examples. For example, although described primarily with respect to application in an implantable embolic protection device, the frame and flow-modulating element structures described herein may find application in a variety of contexts, such as for deflection, separation, or direction of any of a variety of particles or fluids (liquids or gases). As one example, the frame and flow-modulating element structures described herein may be used for deflection, separation, or direction of agricultural materials, such as grain or seed, or for deflection, separation, or direction of oil and gas, such as for isolating oil from oil sands. These and other examples are within the scope of the following claims.

The invention claimed is:

1. An embolic protection device comprising:
an expandable and substantially cylindrical frame, wherein the frame is configured to expand to engage an inner wall of a blood vessel, wherein the frame defines a longitudinal passageway through the frame when expanded, and wherein the expanded frame includes an inner circumference; and
an embolus-deflection element within and coupled to the frame,
wherein the embolus-deflection element extends around a portion of the inner circumference of the frame less than the entire inner circumference, and extends from the frame into the longitudinal passageway,
wherein the embolus-deflection element comprises a leading, embolus-deflection surface and a trailing surface,
wherein the leading, embolus-deflection surface and the trailing surface form a hydrofoil shape, and
wherein the embolus-deflection element is coupled to the frame such that the leading, embolus-deflection surface faces the predominant flow of blood and is configured to deflect an embolus within the vessel when the embolic protection device is implanted within the vessel.

2. The embolic protection device of claim 1, wherein at least one of the frame or the embolus-deflection element comprises a material capable of self-expansion.

3. The embolic protection device of claim 2, wherein the material comprises nitinol.

4. The embolic protection device of claim 1, wherein the embolus-deflection element and the frame are configured to allow blood to pass through the frame in a direction generally transverse to the longitudinal passageway.

5. The embolic protection device of claim 1, wherein the leading, embolus-deflection surface is oriented at an angle with respect to a longitudinal axis of the longitudinal passageway and the trailing surface is oriented at an angle with respect to the longitudinal axis of the longitudinal passageway, and wherein the angle of the leading, embolus-deflection surface and the angle of the trailing surface are selected to minimize turbulent blood flow.

6. The embolic protection device of claim 5, wherein the angle of the leading, embolus-deflection surface relative to the longitudinal axis is greater than the angle of the trailing surface relative to the longitudinal axis.

7. The embolic protection device of claim 5, wherein the angle of the leading, embolus-deflection surface and the angle of the trailing surface are different from each other.

8. The embolic protection device of claim 1, wherein the longitudinal passageway and the embolus-deflection element are sized to allow passage of instruments for at least one of an aortic valve procedure or a proximal vascular procedure including endocardial or coronary targets.

9. The embolic protection device of claim 1, wherein a peak is formed where the leading, embolus-deflection surface and the trailing surface meet, the peak configured to modulate the flow of blood within the vessel when the embolic protection device is implanted within the vessel while minimizing turbulent blood flow, and wherein the leading, embolus-deflection surface, the trailing surface, and the peak form the hydrofoil shape.

10. The embolic protection device of claim 1, wherein the frame is fenestrated.

11. The embolic protection device of claim 1, further comprising:
a plurality of embolus-deflection elements within the frame, wherein the plurality of embolus-deflection elements comprises the embolus-deflection element that extends around the portion of the inner circumference of the frame less than the entire inner circumference and comprises the leading surface and the trailing surface,
wherein the embolus-deflection elements are spaced apart and located at respective longitudinal positions along the frame, and wherein the spacing apart of the embolus-deflection elements allows blood to pass between the embolus-deflection elements and through the frame in a direction generally transverse to the longitudinal passageway, and
wherein the embolus-deflection elements are configured to deflect emboli and direct the emboli through the frame via the longitudinal passageway.

12. The embolic protection device of claim 11, wherein at least one of the frame or the embolus-deflection elements comprises a material capable of self-expansion.

13. The embolic protection device of claim 11, wherein each of the embolus-deflection elements comprises a deflective surface configured to face the predominant flow of blood within the vessel when the embolic protection device is implanted within the vessel.

14. The embolic protection device of claim 13, wherein each of the deflective surfaces is oriented at an angle between about ten degrees and about 80 degrees with respect to a longitudinal axis of the longitudinal passageway.

15. The embolic protection device of claim 13, wherein the frame comprises a plurality of linked elements, and the deflective surfaces are formed on at least some of the linked elements.

16. The embolic protection device of claim 13, wherein each of the deflective surfaces defines a frustum of a cone having a first end with a first diameter and a second end with a second, smaller diameter, wherein the second diameters are configured to provide the longitudinal passageway through the frame.

17. The embolic protection device of claim 13, wherein the deflective surfaces are absent from a portion of the inner circumference of the frame.

18. The embolic protection device of claim 11, wherein the embolus-deflection elements are hydrofoil in shape.

19. The embolic protection device of claim 11, wherein the embolus-deflection elements are arranged in a substantially radially symmetric pattern within the frame.

20. The embolic protection device of claim 11, wherein the embolus-deflection elements are arranged in a substantially radially asymmetric pattern within the frame.

21. The embolic protection device of claim 11, wherein the plurality of embolus-deflection elements comprises at least three embolus-deflection elements.

22. The embolic protection device of claim 11, wherein the longitudinal passageway is sized to allow passage of instruments for at least one of an aortic valve procedure or a proximal vascular procedure including endocardial or coronary targets.

* * * * *